(12) United States Patent
Ke et al.

(10) Patent No.: US 9,085,621 B2
(45) Date of Patent: Jul. 21, 2015

(54) ANTI-IL-1β ANTIBODIES

(75) Inventors: Yaohuang Ke, San Francisco, CA (US); Sum Wai Pierre Lee, San Francisco, CA (US); Yongke Zhang, Palo Alto, CA (US)

(73) Assignee: Apexigen, Inc., Burlingame, CA (US)

( * ) Notice: Subject to any disclaimer, the term of this patent is extended or adjusted under 35 U.S.C. 154(b) by 306 days.

(21) Appl. No.: 13/821,942

(22) PCT Filed: Sep. 9, 2011

(86) PCT No.: PCT/US2011/051035
§ 371 (c)(1),
(2), (4) Date: Aug. 13, 2013

(87) PCT Pub. No.: WO2012/034039
PCT Pub. Date: Mar. 15, 2012

(65) Prior Publication Data
US 2013/0330355 A1 Dec. 12, 2013

Related U.S. Application Data

(60) Provisional application No. 61/381,883, filed on Sep. 10, 2010.

(51) Int. Cl.
C07K 16/24 (2006.01)
A61K 39/395 (2006.01)
A61K 39/00 (2006.01)

(52) U.S. Cl.
CPC ............ *C07K 16/244* (2013.01); *C07K 16/245* (2013.01); *A61K 2039/505* (2013.01); *C07K 2317/24* (2013.01); *C07K 2317/73* (2013.01); *C07K 2317/76* (2013.01); *C07K 2317/92* (2013.01)

(58) Field of Classification Search
CPC .................. C07K 16/244; A61K 2039/505
USPC .............. 424/133.1, 141.1, 145.1; 530/388.1, 530/388.23
See application file for complete search history.

(56) References Cited

U.S. PATENT DOCUMENTS

| | | | |
|---|---|---|---|
| 3,896,111 A | 7/1975 | Kupchan et al. |
| 4,137,230 A | 1/1979 | Hashimoto et al. |
| 4,151,042 A | 4/1979 | Higashide et al. |
| 4,237,224 A | 12/1980 | Cohen et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,751,180 A | 6/1988 | Cousens et al. |
| 4,935,233 A | 6/1990 | Bell et al. |
| 4,946,778 A | 8/1990 | Ladner et al. |
| 5,091,513 A | 2/1992 | Huston et al. |
| 5,132,405 A | 7/1992 | Huston et al. |
| 5,151,510 A | 9/1992 | Stec et al. |
| 5,208,020 A | 5/1993 | Chari et al. |
| 5,264,586 A | 11/1993 | Nicolaou et al. |
| 5,416,064 A | 5/1995 | Chari et al. |
| 5,675,063 A | 10/1997 | Knight |
| 5,712,374 A | 1/1998 | Kuntsmann et al. |
| 5,714,586 A | 2/1998 | Kunstmann et al. |
| 5,773,001 A | 6/1998 | Hamann et al. |
| 5,837,458 A | 11/1998 | Minshull et al. |
| 6,528,624 B1 | 3/2003 | Idusogie et al. |
| 6,538,124 B1 | 3/2003 | Idusogie et al. |
| 6,765,087 B1 | 7/2004 | Casterman et al. |
| 6,838,254 B1 | 1/2005 | Hamers et al. |
| 7,297,775 B2 | 11/2007 | Idusogie et al. |
| 7,317,091 B2 | 1/2008 | Lazar et al. |
| 7,364,731 B2 | 4/2008 | Idusogie et al. |
| 7,429,487 B2 | 9/2008 | Pytela et al. |

(Continued)

FOREIGN PATENT DOCUMENTS

| EP | 0 425 235 | 5/1991 |
|---|---|---|
| WO | WO 81/01145 | 4/1981 |

(Continued)

OTHER PUBLICATIONS

Jackson, et al., "In vitro antibody maturation. Improvement of a high affinity, neutralizing antibody against IL-1 beta," The Journal of Immunology, 154(7):3310-3319, 1995.
Mitroulis, et al., "Targeting IL-1beta in disease; the expanding role of NLRP3 inflammasome," European Journal of Internal Medicine, 21(3):157-163, 2010.
Owyang, et al., "Sa.56. Efficacy of XOMA 052 Antil-II-1beta Antibody in the DBA/1 Mouse Collagen-Induced Arthritis Model," Clinical Immunology, 127:S98-S99, 2008.
Sun, et al., "Design principles for cytokine-neutralizing gels: Cross-linking effects," Acta Biomaterialia, 6(12):4708-4715, 2010.
International Search Report for PCT/US2011/051035, mailed on Jun. 1, 2012.
Written Opinion for PCT/US2011/051035, mailed on Jun. 1, 2012.
International Preliminary Report on Patentability for PCT/US2011/051035, dated Mar. 12, 2013.
Abramson et al., "Blocking the effects of IL-1 in rheumatoid arthritis protects bone and cartilage," *Rheumatology (Oxford)*, 41(9):972-980, (2002).

(Continued)

*Primary Examiner* — Prema Mertz
(74) *Attorney, Agent, or Firm* — Cooley LLP

(57) ABSTRACT

The present invention provides anti-IL-1β monoclonal antibodies and related compositions, which may be used in any of a variety of therapeutic methods for the treatment of inflammatory and other diseases.

13 Claims, 5 Drawing Sheets

(56) References Cited

U.S. PATENT DOCUMENTS

| | | | |
|---|---|---|---|
| 7,462,697 | B2 | 12/2008 | Couto et al. |
| 7,657,380 | B2 | 2/2010 | Lazar et al. |
| 7,662,925 | B2 | 2/2010 | Lazar et al. |
| 7,740,847 | B2 | 6/2010 | Allan et al. |
| 7,744,865 | B2 | 6/2010 | Masat |
| 2003/0026806 | A1 | 2/2003 | Witte |
| 2008/0131435 | A1 | 6/2008 | Stavenhagen et al. |
| 2008/0138344 | A1 | 6/2008 | Stavenhagen et al. |
| 2009/0092599 | A1 | 4/2009 | Lazar et al. |
| 2009/0226421 | A1 | 9/2009 | Parren et al. |
| 2010/0166750 | A1 | 7/2010 | Gram |

FOREIGN PATENT DOCUMENTS

| | | |
|---|---|---|
| WO | WO 88/07378 | 10/1988 |
| WO | WO 92/01047 | 1/1992 |
| WO | WO 93/11161 | 6/1993 |
| WO | WO 93/21232 | 10/1993 |
| WO | WO 94/13804 | 6/1994 |
| WO | WO 95/01997 | 1/1995 |
| WO | WO 01/53353 | 7/2001 |
| WO | WO 2004/063351 | 7/2004 |
| WO | WO 2004/067568 | 8/2004 |
| WO | WO 2006/079372 | 8/2006 |
| WO | WO 2006/081139 | 8/2006 |
| WO | WO 2006/088494 | 8/2006 |
| WO | WO 2006/105338 | 10/2006 |
| WO | WO 2007/024249 | 3/2007 |
| WO | WO 2009/149370 | 12/2009 |
| WO | WO 2010/028273 | 3/2010 |
| WO | WO 2012/034039 | 3/2012 |

OTHER PUBLICATIONS

Bresnihan, "Clinical and radiological effects of anakinra in patients with rheumatoid arthritis," *Rheumatology (Oxford)*, 42(suppl2):ii22-ii28 (2003).

Chung et al., "Critical regulation of early Th17 cell differentiation by interleukin-1 signaling," *Immunity*, 30:576-587 (2009).

Cunnane, "The effects of treatment with interleukin-1 receptor antagonist on the inflamed synovial membrane in rheumatoid arthritis," *Rheumatology (Oxford)*, 40(1):62-69 (2001).

Darville and Eizirk, "Cytokine Induction of Fas Gene Expression in Insulin-Producing Cells Requires the Transcription Factors NF-kappaB and C/EBP," *Diabetes*, 50:1741-1748 (2001).

Dayer, "The pivotal role of interleukin-1 in the clinical manifestations of rheumatoid arthritis," *Rheumatology (Oxford)*, 42(suppl 2):ii3-ii10 (2003).

Dinarello The interleukin-1 family: 10 years of discovery, *FASEB J*, 8(15):1314-1325 (1994).

Dinarello, "The IL-1 family and inflammatory diseases," *Clin Exp Rheumatol*, 20:S1-S13 (2002).

Dinarello, "Therapeutic strategies to reduce IL-1 activity in treating local and systemic inflammation," *Curr Opin Pharmacol*, 4:378-385 (2004).

Gabay et al., "IL-1 pathways in inflammation and human diseases," *Nat Rev Rheumatol.*, 6(4):232-241 (2010).

Hoffman et al., "Mutation of a new gene encoding a putative pyrin-like protein causes familial cold autoinflammatory syndrome and Muckle-Wells syndrome," *Nat Genet*, 29:301-305 (2001).

Lachmann et al., "Use of canakinumab in the cryopyrin-associated periodic syndrome," *New Engl J Med*, 360(23):2416-2425 (2009).

Loweth et al., "Human islets of Langerhans express Fas ligand and undergo apoptosis in response to interleukin-1beta and Fas ligation," *Diabetes*, 47:727-732 (1998).

Maedler et al., "Glucose Induces βcell Apoptosis Via Upregulation of the Fas Receptor in Human Islet," *Diabetes*, 50:1683-1690 (2001).

Maedler et al., "Glucose-induced β cell production of IL-1β contributes to glucotoxicity in human pancreatic islets," *J Clin Invest*, 110:851-860 (2002).

Marshak et al., "Impaired beta-cell functions induced by chronic exposure of cultured human pancreatic islets to high glucose," *Diabetes*, 48:1230-1236 (1999).

Martinon, "Gout-associated uric acid crystals activate the NALP3 inflammasome," *Nature*, 440(7081):237-241 (2006).

Muller, "VEGF and the Fab fragment of a humanized neutralizing antibody: crystal structure of the complex at 2.4 A resolution and mutational analysis of the interface," *Structure*, 6:1153-1167 (1998).

Pickersgill et al., "The anti-interleukin-1 in type 1 diabetes action trial—background and rationale," *Diabetes Metab Res Rev*, 25(4):321-324 (2009).

Saueter "The Antiinflammatory Cytokine Interleukin-1 Receptor Antagonist Protects from High-Fat Diet-Induced Hyperglycemia," *Endocrinology*, 149(5):2208-2218 (2008).

Smirnova et al., "Role of the pro-inflammatory cytokines tumor necrosis factor-alpha, interleukin-1 beta, interleukin-6 and interleukin-8 in the pathogenesis of the otis media with effusion," *Eur. Cytokine Netw.*, 13(2):161-172 (2002).

Smolen and Steiner, "Therapeutic strategies for rheumatoid arthritis," *Nat Rev Drug Discov*, 2:473-488 (2003).

So "A pilot study of IL-1 inhibition by anakinra in acute gout," *Arthritis Res Ther*, 9:R28 (2007).

Yasothan, "Therapies for COPD," *Nat Rev Drug Discov*, 7:285 (2008).

HEAVY chain:

19VH: rabbit antibody HC sequence
3-66: humanization template (human germline)
HZD_H: humanized sequence

```
                 1         2          ==CDR1==    4          =========CDR2=======    7             8              9      ======CDR3======       11
        12345678901234567890abc345678901ab234567890123456789012abc345678901234567890123456789012abc345678901234567890abcdefghiyz1234567890123
19VH    _QSVEESGGRLVTPGTPLILTCTVSGFSLDV--YTVTWVRQAPGKGLEWIGYIW---SGGSASYASWAKGRFTISKTST--TVDLKISSPTTEDTATYFCARVKMISNIE_      TFDPWGPGTLVTVSS
3-66     EVQLVESGGGLVQPGGSLRLSCAASGFTVSS-NYMSWVRQAPGKGLEWVSVIY---SGGSTYYADSVKGRFTISRDNSKNTLYLQMNSLRAEDTAVYYCAR---------     NWFDPWGQGTLVTVSS
HZD-H    EVQLVESGGGLVQPGGSLRLSCAVSGFSLDV--YTMTWVRQAPGKGLEWIGYIW---SGGSASYASWAKGRFTISKDSSKNTVYLQINSLRAEDTAVYFCARVKMISNIE       TFDPWGPGTLVTVSS
```

LIGHT chain:

19VK: rabbit antibody LC sequence
L-19: humanization template (human germline)
HZD_VK: humanized sequence

```
                  1          2         ===CDR1==========    4            ==CDR2=       6             7            8         =====CDR3====    10
         1234567890123456789012345678901234567890abcdef12345678901234567890123456789012345678901234567890123456789012345abcde67890123456 7
19VK    :AYDMTQTPASVEVVGGTVTIKCQASERIY------SGLAWYQQKPGQRPKLLIYRASTLASGVPSRFSGSGSGTEFTLTISDLECADAATYYCHQGVSSSDID_ NVFGGGTEVVVK
L19     :DIQMTQSPSSVSASVGDRVTITCRASQGIS------SWLAWYQQKPGKAPKLLIYAASSLQSVPSRFSGSGSGTDFTLTISSLQPEDFATYYCQQANSFP----LTFGGGTKVEIK
HZD_VK: DIQMTQSPSSVSASVGDRVTIKCQASERIY------SGLAWYQQKPGKRPKLLIYRASTLASGVPSRFSGSGSGTDFTLTISSLQPEDFATYYCQQGVSSSDID NVFGGGTKVEIK
```

FIG. 1

SEQUENCE LISTING

<160> NUMBER OF SEQ ID NOS: 14

<210> SEQ ID NO 1
<211> LENGTH: 117
<212> TYPE: PRT
<213> ORGANISM: Oryctolagus cuniculus

<400> SEQUENCE: 1

Gln Ser Val Glu Glu Ser Gly Gly Arg Leu Val Thr Pro Gly Thr Pro
1               5                   10                  15

Leu Ile Leu Thr Cys Thr Val Ser Gly Phe Ser Leu Asp Val Tyr Thr
            20                  25                  30

Val Thr Trp Val Arg Gln Ala Pro Gly Lys Gly Leu Glu Trp Ile Gly
        35                  40                  45

Tyr Ile Trp Ser Gly Gly Ser Ala Ser Tyr Ala Ser Trp Ala Lys Gly
    50                  55                  60

Arg Phe Thr Ile Ser Lys Thr Ser Thr Thr Val Asp Leu Lys Ile Ser
65                  70                  75                  80

Ser Pro Thr Thr Glu Asp Thr Ala Thr Tyr Phe Cys Ala Arg Val Lys
                85                  90                  95

Met Ile Ser Asn Ile Glu Thr Phe Asp Pro Trp Gly Pro Gly Thr Leu
            100                 105                 110

Val Thr Val Ser Ser
        115

<210> SEQ ID NO 2
<211> LENGTH: 110
<212> TYPE: PRT
<213> ORGANISM: Oryctolagus cuniculus

<400> SEQUENCE: 2

Ala Tyr Asp Met Thr Gln Thr Pro Ala Ser Val Glu Val Val Val Gly
1               5                   10                  15

Gly Thr Val Thr Ile Lys Cys Gln Ala Ser Glu Arg Ile Tyr Ser Gly
            20                  25                  30

Leu Ala Trp Tyr Gln Gln Lys Pro Gly Gln Arg Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys His Gln Gly Val Ser Ser Ser Asp
                85                  90                  95

Ile Asp Asn Val Phe Gly Gly Gly Thr Glu Val Val Val Lys
            100                 105                 110

<210> SEQ ID NO 3
<211> LENGTH: 6
<212> TYPE: PRT
<213> ORGANISM: Oryctolagus cuniculus

<400> SEQUENCE: 3

Asp Val Tyr Thr Val Thr
1               5

<210> SEQ ID NO 4

```
<211> LENGTH: 16
<212> TYPE: PRT
<213> ORGANISM: Oryctolagus cuniculus

<400> SEQUENCE: 4

Tyr Ile Trp Ser Gly Gly Ser Ala Ser Tyr Ala Ser Trp Ala Lys Gly
1               5                   10                  15

<210> SEQ ID NO 5
<211> LENGTH: 13
<212> TYPE: PRT
<213> ORGANISM: Oryctolagus cuniculus

<400> SEQUENCE: 5

Arg Val Lys Met Ile Ser Asn Ile Glu Thr Phe Asp Pro
1               5                   10

<210> SEQ ID NO 6
<211> LENGTH: 11
<212> TYPE: PRT
<213> ORGANISM: Oryctolagus cuniculus

<400> SEQUENCE: 6

Gln Ala Ser Glu Arg Ile Tyr Ser Gly Leu Ala
1               5                   10

<210> SEQ ID NO 7
<211> LENGTH: 7
<212> TYPE: PRT
<213> ORGANISM: Oryctolagus cuniculus

<400> SEQUENCE: 7

Arg Ala Ser Thr Leu Ala Ser
1               5

<210> SEQ ID NO 8
<211> LENGTH: 12
<212> TYPE: PRT
<213> ORGANISM: Oryctolagus cuniculus

<400> SEQUENCE: 8

His Gln Gly Val Ser Ser Ser Asp Ile Asp Asn Val
1               5                   10

<210> SEQ ID NO 9
<211> LENGTH: 120
<212> TYPE: PRT
<213> ORGANISM: Oryctolagus cuniculus

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Asp Val Tyr
            20                  25                  30

Thr Met Thr Trp Val Arg Gln Ala Pro Gly Lys Gly Leu Glu Trp Ile
        35                  40                  45

Gly Tyr Ile Trp Ser Gly Gly Ser Ala Ser Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Ile Asn Ser Leu Arg Ala Glu Asp Thr Ala Val Tyr Phe Cys Ala
                85                  90                  95
```

-continued

Arg Val Lys Met Ile Ser Asn Ile Glu Thr Phe Asp Pro Trp Gly Pro
            100                 105                 110

Gly Thr Leu Val Thr Val Ser Ser
        115                 120

<210> SEQ ID NO 10
<211> LENGTH: 110
<212> TYPE: PRT
<213> ORGANISM: Oryctolagus cuniculus

<400> SEQUENCE: 10

Asp Ile Gln Met Thr Gln Ser Pro Ser Ser Val Ser Ala Ser Val Gly
1               5                   10                  15

Asp Arg Val Thr Ile Lys Cys Gln Ala Ser Glu Arg Ile Tyr Ser Gly
            20                  25                  30

Leu Ala Trp Tyr Gln Gln Lys Pro Gly Lys Arg Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Ser Ser Asp
                85                  90                  95

Ile Asp Asn Val Phe Gly Gly Gly Thr Lys Val Glu Ile Lys
            100                 105                 110

<210> SEQ ID NO 11
<211> LENGTH: 6
<212> TYPE: PRT
<213> ORGANISM: Oryctolagus cuniculus

<400> SEQUENCE: 11

Asp Val Tyr Thr Met Thr
1               5

<210> SEQ ID NO 12
<211> LENGTH: 12
<212> TYPE: PRT
<213> ORGANISM: Oryctolagus cuniculus

<400> SEQUENCE: 12

Gln Gln Gly Val Ser Ser Ser Asp Ile Asp Asn Val
1               5                   10

<210> SEQ ID NO 13
<211> LENGTH: 113
<212> TYPE: PRT
<213> ORGANISM: Oryctolagus cuniculus

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

```
Gln Met Asn Ser Leu Arg Ala Glu Asp Thr Ala Val Tyr Tyr Cys Ala
                85                  90                  95

Arg Asn Trp Phe Asp Pro Trp Gly Gln Gly Thr Leu Val Thr Val Ser
            100                 105                 110

Ser

<210> SEQ ID NO 14
<211> LENGTH: 107
<212> TYPE: PRT
<213> ORGANISM: Oryctolagus cuniculus

<400> SEQUENCE: 14

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
                100                 105
```

ANTI-IL-1β ANTIBODIES

CROSS-REFERENCE TO RELATED APPLICATION

This application is a US national phase application of International Patent Application No. PCT/US2011/051035 filed Sep. 9, 2011, which claims the benefit under 35 U.S.C. §119 (e) of U.S. Provisional Application No. 61/381,883, filed Sep. 10, 2010, which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is APEX_011_01WO_ST25.txt. The text file is 8 KB, was created on Sep. 9, 2011, and is being submitted electronically via EFS-Web.

BACKGROUND

1. Technical Field

The present invention relates generally to anti-IL-1β antibodies, compositions and methods of using same. The invention is more specifically related to anti-IL-1β antibodies and their manufacture and use. Such antibodies are useful, for example, in methods for treating any of a variety of inflammatory diseases.

2. Description of the Related Art

The IL-1 gene family comprises the agonist cytokines, IL-1α and IL-1β, the natural IL-1 receptor antagonist (IL-1Ra), and a number of different proteins that directly regulate IL-1 activity. Both IL-1α and IL-1β are synthesized as cytoplasmic precursors. Although IL-1α remains inside the cell, IL-1β is efficiently processed and secreted, making it an attractive target for therapeutic antibodies.

IL-1β is a cytokine produced primarily by monocytes/macrophages following stimulation by bacterial products and immune complexes. In addition, IL-1β is an important mediator of the inflammatory response, and is involved in a variety of cellular activities, including cell proliferation, differentiation, and apoptosis by signaling through NF-κB and c-Jun pathways. IL-1β activates the release of proinflammatory cytokines such as TNF and IL-6, and induces a Th17 bias in the cellular adaptive responses. Excess release of IL-1β has been implicated in autoimmune and inflammatory syndromes characterized by attacks of sterile inflammation of joints, serositis, fever, and skin lesions.

A. IL-1β and Rheumatoid Arthritis (RA)

RA is a chronic inflammatory disease of the joints that is associated with destruction of cartilage and bone. In addition to its local destructive nature, it also can have a pronounced systemic inflammatory component, presenting as fever, headache and fatigue, and may even affect other organs such as the skin, liver, spleen and lymph nodes.

IL-1β is a proinflammatory cytokine acting during the autoimmune process. The contribution made by proinflammatory cytokines such as tumour necrosis factor (TNF)-α and IL-1 has been validated in preclinical animal models and in human RA patients (Dinarello 2002). IL-1β plays a key role in driving joint inflammation and destruction in RA. For example, in RA patients, IL-1β is overexpressed in inflamed synovial tissue, particularly in the lining layer and in sublining cells. IL-1β expression is elevated in draining lymph nodes from affected joints (Dayer 2003). In addition, cartilage from RA patients exhibits upregulation of IL-1β mRNA as compared with normal cartilage. Furthermore, an increased level of IL-1β in synovial fluid has been found to correlate with histological features of RA. Further still, treatment with IL-1Ra (Anakinra, Amgen) improved pathological changes in RA joints (Cunnane 2001) and delayed the progression of joint damage (Bresnihan 2003). This product was approved for treating patients with moderate to severe rheumatoid arthritis who have inadequate responses to conventional disease-modifying antirheumatic drug (DMARD) therapy. An antibody against IL-1β (Canakinumab, Novatis) administrated to methotrexate refractory patients resulted in clinical improvement in ACR20 scores.

B. IL-1β and Diabetes

Type 1 diabetes mellitus is a form of diabetes mellitus that results from autoimmune destruction of insulin-producing β cells of the pancreas. The subsequent lack of insulin leads to increased blood and urine glucose. IL-1β is a proinflammatory cytokine acting during the autoimmune process of type 1 diabetes. For example, IL-1β inhibits β cell function and promotes Fas-triggered apoptosis of β cells by activating transcription factor NF-κB (Pickersgill 2009).

Type 2 diabetes mellitus is a metabolic disorder that is characterized by high blood glucose in the context of insulin resistance and relative insulin deficiency. Chronic elevation of blood glucose (hyperglycemia) induces pancreatic β cell apoptosis by upregulation of Fas (Maedler 2001). This further impairs β cell function, leading to glucotoxicity (Marshak 1999). IL-1β has been implicated in the pathogenesis of type II diabetes. For example, high glucose levels resulted in increased production and release of IL-1β, leading to NF-κB activation, Fas upregulation, DNA fragmentation, and impaired β cell function. (Maedler 2002). IL-1Ra (Anakinra, Amgen) treatment has been shown to prevent hyperglycemia by improving glucose tolerance and insulin secretion in the diet-induced obesity model of Type 2 diabetes (Sauter 2008).

C. IL-1β and Gout

Gout is caused by abnormal purine metabolism and is associated with deposition of mono sodium urate (MSU) crystals in joints and peri articular tissues. Similarly, pseudogout arises from deposition of calcium pyrophosphate dehydrate crystals, owing to unknown causes. Supporting evidence of IL-1β involvement of Gout includes, for example, MSU and calcium pyrophosphate dihydrate crystals activated the NALP3 inflammasome, which causes the production of active IL-1β (Martinon 2006). In addition, blocking IL-1β reduced MSU-crystal-induced inflammation in a mouse model. Further, gout patients who failed to respond to standard anti-inflammatory therapies respond well to the treatment with 100 mg/day of Anakinra. Finally, antibody against IL-1β provides superior pain relief with a more rapid onset compared with triamcinolone acetonide for acute flares in patients with gouty arthritis that are refractory to nonsteroidal anti-inflammatory drugs (So 2007).

D. IL-1β and Cryopyrin-Associated Periodic Syndrome (CAPS)

CAPS comprises a spectrum of apparently distinct, rare, inherited inflammatory disorders of increasing severity, including the familial cold autoinflammatory syndrome, the Muckle-Wells syndrome, and neonatal-onset multisystem inflammatory disorder. The majority of these disorders, caused by missense mutations in the NACHT domain of the NALP3/CIAS1 gene, are prime examples of dysregulated processing and secretion of IL-1β.

Despite the known involvement of IL-1β in these and other disease conditions, there remains an important need for more potent humanized monoclonal antibodies that neutralize IL-1β activities and inhibits IL-1β downstream signaling, thereby preventing IL-1β-associated cytokine production and inflammatory diseases. The present invention addresses these needs and offers other related advantages.

BRIEF SUMMARY

One aspect of the present disclosure provides an isolated antibody, or an antigen-binding fragment thereof, that binds to IL-1β, comprising (i) a heavy chain variable region comprising the VHCDR1 region set forth in SEQ ID NO:3, the VHCDR2 region set forth in SEQ ID NO:4, and the VHCDR3 region set forth SEQ ID NO:5; and (ii) a light chain variable region comprising the VLCDR1 region set forth in SEQ ID NO:6, the VLCDR2 region set forth in SEQ ID NO:7, and the VLCDR3 region set forth in SEQ ID NO: 8; or a variant of said antibody, or an antigen-binding fragment thereof, comprising heavy and light chain variable regions identical to the heavy and light chain variable regions of (i) and (ii) except for up to 8 amino acid substitutions in said CDR regions. In one embodiment of the antibodies disclosed herein, the heavy chain variable region comprises the amino acid sequence set forth in SEQ ID NO:1. In another embodiment, the light chain variable region comprises the amino acid sequence set forth in SEQ ID NO:2.

Another aspect of the present disclosure provides an isolated antibody, or an antigen-binding fragment thereof, that binds to IL-1β, comprising a heavy chain variable region comprising the amino acid sequence set forth in SEQ ID NO:1. In one embodiment of this aspect, the isolated antibody, or antigen-binding fragment thereof comprises a light chain variable region which comprises an amino acid sequence having at least 90% identity to the amino acid sequence set forth in SEQ ID NO:2. In a further embodiment of this aspect, the isolated antibody, or an antigen-binding fragment thereof comprises a light chain variable region which comprises the amino acid sequence set forth in SEQ ID NO:2.

Yet a further aspect of the present disclosure provides an isolated antibody, or an antigen-binding fragment thereof, that binds to IL-1β, comprising a light chain variable region comprising the amino acid sequence set forth in SEQ ID NO:2. In one embodiment of this aspect, the isolated antibody, or antigen binding fragment thereof comprises a heavy chain variable region which comprises an amino acid sequence having at least 90% identity to the amino acid sequence set forth in SEQ ID NO:1.

In certain embodiments, the isolated antibodies as disclosed herein are humanized. Illustrative humanized antibody variable regions are set forth in the VH region amino acid sequence of SEQ ID NO:9 and the VL region amino acid sequence of SEQ ID NO:10.

In one embodiment, an isolated antibody disclosed herein may be single chain antibody, a ScFv, a univalent antibody lacking a hinge region, a minibody, a Fab, a Fab' fragment, or a F(ab')$_2$ fragment. In certain embodiments, the antibodies herein are whole antibodies.

In another embodiment, the isolated antibodies as described herein comprise a human IgG constant domain, such as, but not limited to an IgG1 CH1 domain or an IgG1 Fc region.

A further embodiment of the disclosure provides an isolated antibody, or an antigen-binding fragment thereof, that competes with the anti-IL-1β antibodies described herein for binding to IL-1β.

In one embodiment of this disclosure, the isolated antibody, or antigen-binding fragment thereof, that binds IL-1β, binds with a KD of 0.199 nM or lower.

The present disclosure also provides isolated polynucleotides encoding the isolated antibodies, or antigen-binding fragments thereof as disclosed herein. In another embodiment, the present disclosure provides expression vectors comprising the isolated polynucleotides encoding the isolated antibodies, or antigen-binding fragments thereof as disclosed herein, and isolated host cells comprising such vectors.

The present disclosure also provides compositions comprising a physiologically acceptable carrier and a therapeutically effective amount of an anti-IL-1β antibody or antigen-binding fragment thereof as described herein.

In another embodiment, the present disclosure provides methods for treating a patient having a disease associated with aberrant IL-1β expression, comprising administering to the patient the compositions comprising a physiologically acceptable carrier and a therapeutically effective amount of an anti-IL-1β antibody or antigen-binding fragment thereof, thereby treating the disease associated with aberrant IL-1β expression. In this regard, diseases associated with associated with aberrant IL-1β expression include but are not limited to rheumatoid arthritis, diabetes, Cryopyrin-associated periodic syndrome, gout, chronic obstructive pulmonary disorder, atherosclerosis and vasculitis.

The present invention provides anti-IL-1β antibody amino acid sequences, as well as polynucleotides encoding such antibodies and compositions comprising the same. The identification of the DNA sequences encoding anti-IL-1β antibodies, and the amino acid sequences of such antibodies, permits the production of potent recombinant anti-IL-1β antibodies at high yields, for use in the treatment of various inflammatory diseases.

Therefore, according to certain embodiments, the present invention provides an isolated polypeptide capable of specifically binding human IL-1β, comprising an amino acid sequence selected from the group consisting of:

(a) an anti-IL-1β antibody sequence set forth in FIG. 1;

(b) a sequence having at least 90% identity to an anti-IL-1β antibody sequence set forth in FIG. 1;

(c) an FR domain of an anti-IL-1β antibody sequence set forth in FIG. 1;

(d) a CDR domain of an anti-IL-1β antibody sequence set forth in FIG. 1; and (e) a sequence consisting of at least 5 contiguous residues of the variable region of an anti-IL-1β antibody sequence set forth in FIG. 1.

The invention, in another aspect, provides isolated polynucleotides encoding a polypeptide as set forth above and/or described herein, as well as expression vectors and host cells containing the same.

In certain more specific embodiments, the invention provides an isolated monoclonal antibody comprising at least a portion of an IL-1β antibody sequence as described herein, such as an IL-1β antibody sequence set forth in FIG. 1, wherein the isolated monoclonal antibody specifically binds IL-1β. It will be understood, of course, that an antibody of the invention may be a humanized antibody or a binding fragment or variant thereof.

In another specific embodiment, the invention provides an isolated antibody that specifically binds to IL-1β and comprises at least the CDR region of an anti-IL-1β antibody sequence set forth in FIG. 1.

In yet another embodiment, the invention provides an isolated single chain variable fragment antibody that specifically binds to IL-1β and comprises at least the CDR region of an anti-IL-1β antibody sequence set forth in FIG. 1.

According to another aspect of the invention, there is provided a method for treating a disease mediated by IL-1β comprising administering to a subject in need thereof a therapeutically effective amount of an IL-1β binding polypeptide or antibody sequence described herein. In certain embodiments, the disease treated according to this method is an inflammatory disease or a cardiovascular disease. In certain more specific embodiments, the disease is selected from the group consisting of rheumatoid arthritis, diabetes, gout, cryopyrin-associated periodic syndrome, chronic obstructive pulmonary disorder and various cardiovascular diseases such as atherosclerosis and vasculitis.

BRIEF DESCRIPTION OF THE SEVERAL VIEWS OF THE DRAWINGS

FIG. 1 shows the heavy and light chain variable regions of an exemplary humanized anti-IL-1β antibody (SEQ ID NOs:1 and 2, respectively), with the CDR sequences indicated. The humanized heavy and light chain variable region sequences are shown in bold (SEQ ID NOs:9 and 10, respectively). The human germline VH and VL sequences shown are set forth in SEQ ID NOs:13 and 14, respectively.

BRIEF DESCRIPTION OF THE SEQUENCES

Figure 2:
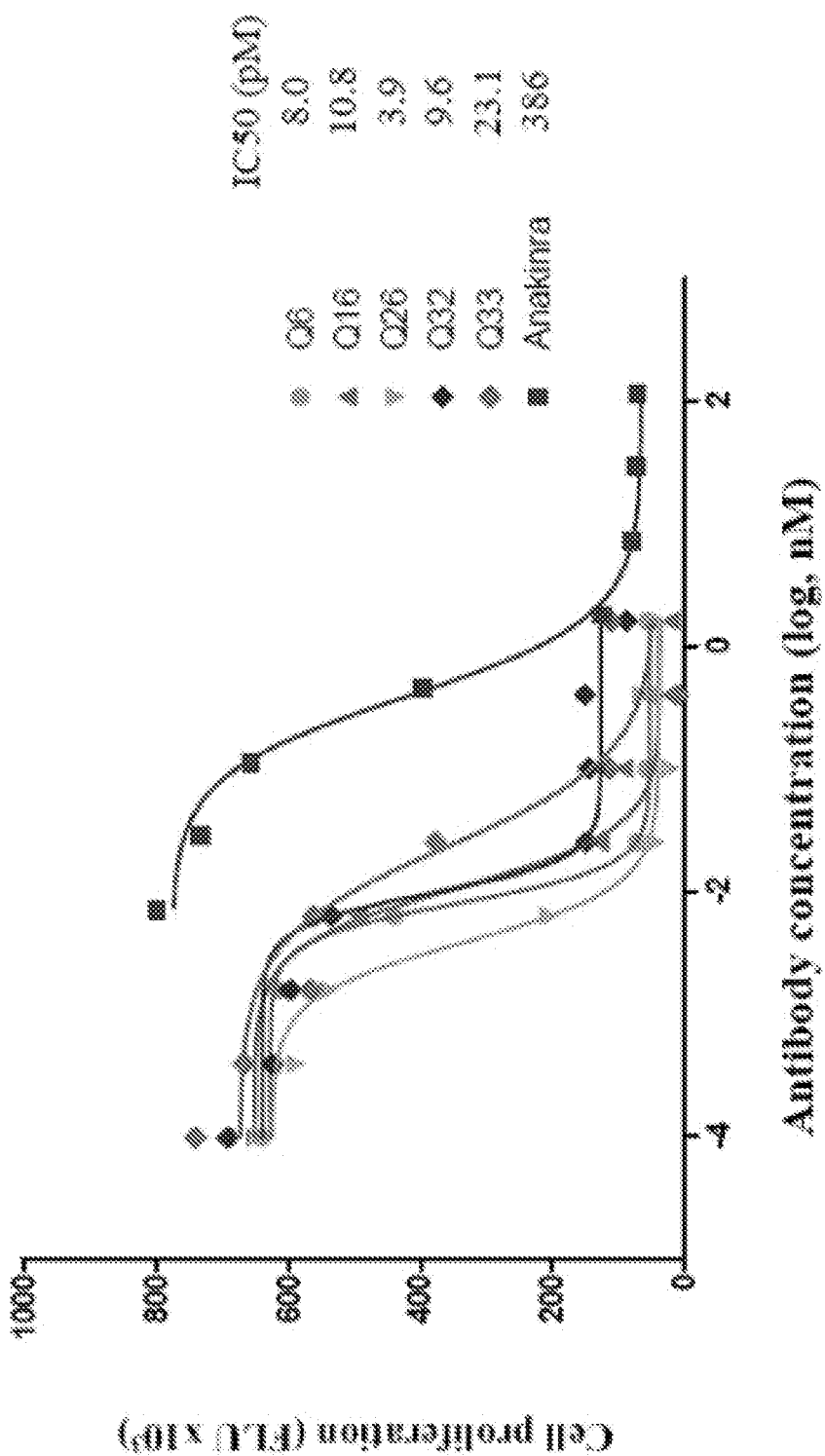
FIG. 2 shows the dose dependent inhibition of IL-1-β-induced TF-1 cell proliferation by anti-IL-1-β antibodies.

SEQ ID NO:1 is the amino acid sequence of the VH region of the clone Q26 rabbit anti-IL-1β antibody.

SEQ ID NO:2 is the amino acid sequence of the VL region of the clone Q26 rabbit anti-IL-1β antibody.

SEQ ID NO:3 is the amino acid sequence of the VHCDR1 region of the clone Q26 rabbit anti-IL-1β antibody.

SEQ ID NO:4 is the amino acid sequence of the VHCDR2 region of the clone Q26 rabbit anti-IL-1β antibody.

SEQ ID NO:5 is the amino acid sequence of the VHCDR3 region of the clone Q26 rabbit anti-IL-1β antibody.

SEQ ID NO:6 is the amino acid sequence of the VLCDR1 region of the clone Q26 rabbit anti-IL-1β antibody.

SEQ ID NO:7 is the amino acid sequence of the VLCDR2 region of the clone Q26 rabbit anti-IL-1β antibody.

SEQ ID NO:8 is the amino acid sequence of the VLCDR3 region of the clone Q26 rabbit anti-IL-1β antibody.

SEQ ID NO:9 is the amino acid sequence of the humanized sequence of the VH region of the clone Q26 rabbit anti-IL-1β antibody.

SEQ ID NO:10 is the amino acid sequence of the humanized sequence of the VL region of the clone Q26 rabbit anti-IL-1β antibody.

SEQ ID NO:11 is the humanized sequence of the VHCDR1 of the clone Q26 rabbit anti-IL-1β antibody.

SEQ ID NO:12 is the humanized sequence of the VLCDR3 of the clone Q26 rabbit anti-IL-1β antibody.

SEQ ID NO:13 is the VH human germline sequence used for humanization of the Q26 rabbit anti-IL-1β antibody clone.

SEQ ID NO:14 is the VL human germline sequence used for humanization of the Q26 rabbit anti-IL-1β antibody clone.

DETAILED DESCRIPTION

The present disclosure relates to antibodies and antigen-binding fragments thereof the specifically bind to IL-1β, in particular antibodies having specific epitopic specificity and functional properties. One embodiment of the invention encompasses specific humanized antibodies and fragments thereof capable of binding to IL-1β, blocking IL-1β binding with the IL-1β receptor and inhibiting IL-1β-induced downstream cell signaling and biological effects. In more specific embodiments of the invention, the antibodies described herein specifically bind to IL-1β with high affinity and block IL-1β binding to its receptor.

Embodiments of the invention pertain to the use of anti-IL-1β antibodies or antigen-binding fragments thereof for the diagnosis, assessment and treatment of diseases and disorders associated with IL-1β, the IL-1β receptor or aberrant expression thereof. The subject antibodies are used in the treatment or prevention of inflammatory and autoimmune diseases including rheumatoid arthritis, diabetes, gout, cryopyrin-associated periodic syndrome (CAPS) and chronic obstructive pulmonary disorder (COPD), among other diseases.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); Transcription and Translation (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Embodiments of the present invention relate to antibodies that bind to the IL-1β. In particular, the antibodies described herein specifically bind to IL-1β with unexpectedly high affinity, block receptor binding to the IL-1β, block receptor activity and have therapeutic utility for the treatment of diseases associated with aberrant expression IL-1β or the IL-1β receptor. The antibodies described herein also have advantageous properties such as the ability to inhibit a variety of IL-1β-mediated biological effects (e.g., cell proliferation, differentiation, the release of proinflammatory cytokines such as TNF and IL-6, and apoptosis by signaling through NF-kB and c-Jun pathways), and other IL-1β-mediated effects known to the skilled person). The antibodies described herein may also have effects on IL-1β receptor internalisation.

Sequences of illustrative antibodies, or antigen-binding fragments, or complementarity determining regions (CDRs) thereof, are set forth in SEQ ID NOs:1-12 (see also FIG. 1).

As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein, the term encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. "Diabodies", multivalent or multispecific fragments constructed by gene fusion (WO94/13804; P. Holliger et al., Proc. Natl. Acad. Sci. USA 90 6444-6448, 1993) are also a particular form of antibody contemplated herein. Minibodies comprising a scFv joined to a CH3 domain are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883, 1988); PCT/US92/09965; WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "antigen-binding fragment" as used herein refers to a polypeptide fragment that contains at least one CDR of an immunoglobulin heavy and/or light chains that binds to the antigen of interest, in particular to the IL-1β. In this regard, an antigen-binding fragment of the herein described antibodies may comprise 1, 2, 3, 4, 5, or all 6 CDRs of a VH and VL sequence set forth herein from antibodies that bind IL-1β. An antigen-binding fragment of the IL-1β-specific antibodies described herein is capable of binding to IL-1β. In certain embodiments, an antigen-binding fragment or an antibody comprising an antigen-binding fragment, prevents or inhibits binding of IL-1β to its receptor and subsequent signaling events. In certain embodiments, the antigen-binding fragment binds specifically to and/or inhibits or modulates the biological activity of human IL-1β.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is ≤$10^{-7}$ or $10^{-8}$ M. In some embodiments, the equilibrium dissociation constant may be ≤$10^{-9}$ M or ≤$10^{-10}$ M.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

In certain embodiments, single chain Fv or scFV antibodies are contemplated. For example, Kappa bodies (III et al., *Prot. Eng.* 10: 949-57 (1997); minibodies (Martin et al., *EMBO J.* 13: 5305-9 (1994); diabodies (Holliger et al., *PNAS* 90: 6444-8 (1993); or Janusins (Traunecker et al., *EMBO J.* 10: 3655-59 (1991) and Traunecker et al., *Int. J. Cancer Suppl.* 7: 51-52 (1992), may be prepared using standard molecular biology techniques following the teachings of the present application with regard to selecting antibodies having the desired specificity. In still other embodiments, bispecific or chimeric antibodies may be made that encompass the ligands of the present disclosure. For example, a chimeric antibody may comprise CDRs and framework regions from different antibodies, while bispecific antibodies may be generated that bind specifically to IL-1β through one binding domain and to a second molecule through a second binding domain. These antibodies may be produced through recombinant molecular biological techniques or may be physically conjugated together.

A single chain Fv (sFv) polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, an IL-1β binding antibody as described herein is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

A dAb fragment of an antibody consists of a VH domain (Ward, E. S. et al., Nature 341, 544-546 (1989)).

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al., *Protein Eng.*, 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies of the present disclosure may take the form of a nanobody. Nanobodies are encoded by single genes and are efficiently produced in almost all prokaryotic and eukaryotic hosts e.g. *E. coli* (see e.g. U.S. Pat. No. 6,765,087), moulds (for example *Aspergil-*

*lus* or *Trichoderma*) and yeast (for example *Saccharomyces, Kluyvermyces, Hansenula* or *Pichia* (see e.g. U.S. Pat. No. 6,838,254). The production process is scalable and multi-kilogram quantities of nanobodies have been produced. Nanobodies may be formulated as a ready-to-use solution having a long shelf life. The Nanoclone method (see, e.g., WO 06/079372) is a proprietary method for generating Nanobodies against a desired target, based on automated high-throughput selection of B-cells.

In certain embodiments, the anti-IL-1β antibodies or antigen-binding fragments thereof as disclosed herein are humanized. This refers to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio, A. F. et al., (1989) *Proc Natl Acad Sci USA* 86:4220-4224; Queen et al., *PNAS* (1988) 86:10029-10033; Riechmann et al., *Nature* (1988) 332:323-327). Illustrative methods for humanization of the anti-IL-1β antibodies disclosed herein include the methods described in U.S. Pat. No. 7,462,697. Illustrative humanized antibodies according to certain embodiments of the present invention comprise the humanized sequences provided in SEQ ID NOs:9, 10, 19 and 20.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856. Riechmann, L., et al., (1988) *Nature* 332: 323-327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybridoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present disclosure may be chimeric antibodies. In this regard, a chimeric antibody is comprised of an antigen-binding fragment of an anti-IL-1β antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the anti-IL-1β antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In certain embodiments, an IL-1β-binding antibody comprises one or more of the CDRs of the antibodies described herein. In this regard, it has been shown in some cases that the transfer of only the VHCDR3 of an antibody can be performed while still retaining desired specific binding (Barbas et al., *PNAS* (1995) 92: 2529-2533). See also, McLane et al., *PNAS* (1995) 92:5214-5218, Barbas et al., *J. Am. Chem. Soc.* (1994) 116:2161-2162.

Marks et al (*Bio/Technology*, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds IL-1β. The repertoire may then be displayed in a suitable host system such as the phage display system of WO92/01047 so that suitable antibodies or antigen-binding fragments thereof may be selected. A repertoire may consist of at least from about $10^4$ individual members and upwards by several orders of magnitude, for example, to about from $10^6$ to $10^8$ or $10^{10}$ or more members. Analogous shuffling or combinatorial techniques are also disclosed by Stemmer (Nature, 1994, 370: 389-391), who describes the technique in relation to a β-lactamase gene but observes that the approach may be used for the generation of antibodies.

A further alternative is to generate novel VH or VL regions carrying one or more CDR-derived sequences of the herein described invention embodiments using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al., (1994, Proc. Natl. Acad. Sci., USA, 91:3809-3813) and Schier et al (1996, J. Mol. Biol. 263:551-567).

In certain embodiments, a specific VH and/or VL of the antibodies described herein may be used to screen a library of the complementary variable domain to identify antibodies with desirable properties, such as increased affinity for IL-1β. Such methods are described, for example, in Portolano et al., *J. Immunol.* (1993) 150:880-887; Clarkson et al., Nature (1991) 352:624-628.

Other methods may also be used to mix and match CDRs to identify antibodies having desired binding activity, such as binding to IL-1β. For example: Klimka et al., *British Journal of Cancer* (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antibodies or antigen-binding fragments thereof according to several embodiments of the invention described herein, using routine methodology in the art.

Also disclosed herein is a method for obtaining an antibody antigen binding domain specific for IL-1β antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for IL-1β and optionally with one or more desired properties. The VL domains may have an amino acid sequence which is substantially as set out herein. An analogous method may be employed in which one or more sequence variants of a VL domain disclosed herein are combined with one or more VH domains.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a IL-1β epitope is an antibody that binds one IL-1β epitope with greater affinity, avidity, more readily, and/or with greater duration than it binds to other IL-1β epitopes or non-IL-1β epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439-473.

In certain embodiments, the anti-IL-1β antibodies described herein have an affinity of about 100, 150, 155, 160, 170, 175, 180, 185, 190, 191, 192, 193, 194, 195, 196, 197, 198 or 199 picomolar, and in some embodiments, the antibodies may have even higher affinity for IL-1β.

The term "immunologically active", with reference to an epitope being or "remaining immunologically active", refers to the ability of an antibody (e.g., anti-IL-1β antibody) to bind to the epitope under different conditions, for example, after the epitope has been subjected to reducing and denaturing conditions.

An antibody or antigen-binding fragment thereof according to certain preferred embodiments of the present application may be one that competes for binding to IL-1β with any antibody described herein which both (i) specifically binds to the antigen and (ii) comprises a VH and/or VL domain disclosed herein, or comprises a VH CDR3 disclosed herein, or a variant of any of these. Competition between antibodies may be assayed easily in vitro, for example using ELISA and/or by tagging a specific reporter molecule to one antibody which can be detected in the presence of other untagged antibodies, to enable identification of specific antibodies which bind the same epitope or an overlapping epitope. Thus, there is provided herein a specific antibody or antigen-binding fragment thereof, comprising a human antibody antigen-binding site which competes with an antibody described herein that binds to IL-1β.

In this regard, as used herein, the terms "competes with", "inhibits binding" and "blocks binding" (e.g., referring to inhibition/blocking of binding of IL-1β to its receptor or referring to inhibition/blocking of binding of an anti-IL-1β antibody to IL-1β) are used interchangeably and encompass both partial and complete inhibition/blocking. The inhibition/blocking of IL-1β to its receptor preferably reduces or alters the normal level or type of cell signaling that occurs when IL-1β binds to its receptor without inhibition or blocking. Inhibition and blocking are also intended to include any measurable decrease in the binding of IL-1β to its receptor when in contact with an anti-IL-1β antibody as disclosed herein as compared to the ligand not in contact with an anti-IL-1β antibody, e.g., the blocking of the receptor to IL-1β by at least about 10%, 20%, 30%, 40%, 50%, 60%, 65%, 70%, 75%, 80%, 85%, 90%, 91%, 92%, 93%, 94%, 95%, 96%, 97%, 98%, 99%, or 100%.

The constant regions of immunoglobulins show less sequence diversity than the variable regions, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region.

The Fc region of an antibody interacts with a number of Fc receptors and ligands, imparting an array of important functional capabilities referred to as effector functions. For IgG the Fc region comprises Ig domains CH2 and CH3 and the N-terminal hinge leading into CH2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack.

The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). All FcγRs bind the same region on Fc, at the N-terminal end of the Cg2 (CH2) domain and the preceding hinge. This interaction is well characterized structurally (Sondermann et al., 2001, J Mol Biol 309:737-749), and several structures of the human Fc bound to the extracellular domain of human FcγRIIIb have been solved (pdb accession code 1E4K) (Sondermann et al., 2000, Nature 406:267-273.) (pdb accession codes 1IIS and 1IIX) (Radaev et al., 2001, J Biol Chem 276:16469-16477.)

The different IgG subclasses have different affinities for the FcγRs, with IgG1 and IgG3 typically binding substantially better to the receptors than IgG2 and IgG4 (Jefferis et al., 2002, Immunol Lett 82:57-65). All FcγRs bind the same region on IgG Fc, yet with different affinities: the high affinity binder FcγRI has a Kd for IgG1 of $10^{-8}$ M$^{-1}$, whereas the low affinity receptors FcγRII and FcγRII generally bind at $10^{-6}$ and $10^{-6}$ respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of DEC Pharmaceuticals Corporation). Patients with the V158 allotype respond favorably to rituximab treatment; however, patients with the lower affinity F158 allotype respond poorly (Cartron et al., 2002, Blood 99:754-758). Approximately 10-20% of humans are V158N158 homozygous, 45% are V158/F158 heterozygous, and 35-45% of humans are F158/F158 homozygous (Lehrnbecher et al., 1999, Blood 94:4220-4232; Cartron et al., 2002, Blood 99:754-758). Thus 80-90% of humans are poor responders, that is they have at least one allele of the F158 FcγRIIIa.

The Fc region is also involved in activation of the complement cascade. In the classical complement pathway, C1 binds with its C1q subunits to Fc fragments of IgG or IgM, which has formed a complex with antigen(s). In certain embodiments of the invention, modifications to the Fc region comprise modifications that alter (either enhance or decrease) the ability of an IL-1β-specific antibody as described herein to activate the complement system (see e.g., U.S. Pat. No. 7,740, 847). To assess complement activation, a complement-dependent cytotoxicity (CDC) assay may be performed (See, e.g., Gazzano-Santoro et al., J. Immunol. Methods, 202:163 (1996)).

Thus in certain embodiments, the present invention provides anti-IL-1β antibodies having a modified Fc region with altered functional properties, such as reduced or enhanced CDC, ADCC, or ADCP activity, or enhanced binding affinity for a specific FcγR or increased serum half-life. Other modified Fc regions contemplated herein are described, for example, in issued U.S. Pat. Nos. 7,317,091; 7,657,380; 7,662,925; 6,538,124; 6,528,624; 7,297,775; 7,364,731; Published U.S. Applications US2009092599; US20080131435; US20080138344; and published International Applications WO2006/105338; WO2004/063351; WO2006/088494; WO2007/024249.

Thus, in certain embodiments, antibody variable domains with the desired binding specificities are fused to immunoglobulin constant domain sequences. In certain embodiments, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Antibodies of the present invention (and antigen-binding fragments and variants thereof) may also be modified to include an epitope tag or label, e.g., for use in purification or diagnostic applications. There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

In another contemplated embodiment, a IL-1β-specific antibody as described herein may be conjugated or operably linked to another therapeutic compound, referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforemention therapeutic agents may find use as antibody conjugates.

In an alternate embodiment, the antibody is conjugated or operably linked to a toxin, including but not limited to small molecule toxins and enzymatically active toxins of bacterial, fungal, plant or animal origin, including fragments and/or variants thereof. Small molecule toxins include but are not limited to saporin (Kuroda K, et al., The Prostate 70:1286-1294 (2010); Lip, W L. et al., 2007 Molecular Pharmaceutics 4:241-251; Quadros EV., et al., 2010 Mol Cancer Ther; 9(11); 3033-40; Polito L., et al. British Journal of Haematology, 147, 710-718), calicheamicin, maytansine (U.S. Pat. No. 5,208,020), trichothene, and CC1065. Toxins include but are not limited to RNase, gelonin, enediynes, ricin, abrin, diptheria toxin, cholera toxin, gelonin, *Pseudomonas* exotoxin (PE40), *Shigella* toxin, *Clostridium perfringens* toxin, and pokeweed antiviral protein.

In one embodiment, an antibody or antigen-binding fragment thereof of the disclosure is conjugated to one or more maytansinoid molecules. Maytansinoids are mitototic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

Another conjugate of interest comprises an antibody conjugated to one or more calicheamicin molecules. The calicheamicin family of antibiotics are capable of producing double-stranded DNA breaks at sub-picomolar concentrations. Structural analogues of calicheamicin that may also be used (Hinman et al., 1993, Cancer Research 53:3336-3342; Lode et al., 1998, Cancer Research 58:2925-2928) (U.S. Pat. No. 5,714,586; U.S. Pat. No. 5,712,374; U.S. Pat. No. 5,264, 586; U.S. Pat. No. 5,773,001). Dolastatin 10 analogs such as auristatin E (AE) and monomethylauristatin E (MMAE) may find use as conjugates for the presently disclosed antibodies, or variants thereof (Doronina et al., 2003, Nat Biotechnol 21(7):778-84; Francisco et al., 2003 Blood 102(4):1458-65). Useful enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, PCT WO 93/21232. The present disclosure further contemplates embodiments in which a conjugate or fusion is formed between an IL-1β-specific antibody as described herein and a compound with nucleolytic activity, for example a ribonuclease or DNA endonuclease such as a deoxyribonuclease (DNase).

In an alternate embodiment, a herein-disclosed antibody may be conjugated or operably linked to a radioisotope to form a radioconjugate. A variety of radioactive isotopes are available for the production of radioconjugate antibodies. Examples include, but are not limited to $^{90}$Y, $^{123}$I, $^{125}$I, $^{131}$I, $^{186}$Re, $^{188}$Re, $^{211}$At, and $^{212}$Bi.

Antibodies described herein may in certain other embodiments be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxel/paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. One preferred exemplary cytotoxin is saporin (available from Advanced Targeting Systems, San Diego, Calif.). Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine).

Moreover, a IL-1β-specific antibody (including a functional fragment thereof as provided herein such as an antigen-binding fragment) may in certain embodiments be conjugated to therapeutic moieties such as a radioactive materials or macrocyclic chelators useful for conjugating radiometal ions. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50.

In yet another embodiment, an antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent, see PCT WO 81/01145) to an active anti-cancer drug. See, for example, PCT WO 88/07378 and U.S. Pat. No. 4,975,278. The enzyme component of the immunoconjugate useful for ADEPT includes any enzyme capable of acting on a prodrug in such a way so as to convert it into its more active, cytotoxic form. Enzymes that are useful in the method of these and related embodiments include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as -galactosidase and neuramimidase useful for converting glycosylated prodrugs into free drugs; beta-lactamase useful for converting drugs derivatized with -lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", may be used to convert prodrugs into free active drugs (see, for example, Massey, 1987, Nature 328: 457-458). Antibody-abzyme conjugates can be prepared for delivery of the abzyme to a tumor cell population.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage. The linker may be a "cleavable linker" facilitating release of one or more cleavable components. For example, an acid-labile linker may be used (Cancer Research 52: 127-131 (1992); U.S. Pat. No. 5,208,020).

Other modifications of the antibodies (and polypeptides) of the invention are also contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

The desired functional properties of anti-IL-1β antibodies may be assessed using a variety of methods known to the skilled person such as affinity/binding assays (for example, surface plasmon resonance, competitive inhibition assays); inflammatory or autoimmune response inhibition using in vitro or in vivo models; cytotoxicity assays, cell viability assays, cell proliferation or differentiation assays in response to IL-1β. In certain embodiments, the antibodies herein are assessed by measuring, e.g., IL-1β-induced TF-1 cell proliferation or nuclear translocation of NF-kB. Other assays may test the ability of antibodies described herein to block normal receptor/IL-1β-mediated responses, such as cell proliferation, differentiation, apoptosis by signaling through NF-kB and c-Jun pathways, release of proinflammatory cytokines such as TNF and IL-6, and Th17 bias in cellular adaptive responses. The antibodies described herein may also be tested for effects on IL-1β receptor internalisation, in vitro and in vivo efficacy, etc. Such assays may be performed using well-established protocols known to the skilled person (see e.g., Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or commercially available kits.

The present invention further provides in certain embodiments an isolated nucleic acid encoding an antibody or antigen-binding fragment thereof as described herein, for instance, a nucleic acid which codes for a CDR or VH or VL domain as described herein. Nucleic acids include DNA and RNA. These and related embodiments may include polynucleotides encoding antibodies that bind IL-1β as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phosphoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, the present disclosure also provides polynucleotides encoding the anti-IL-1β antibodies described herein. In certain embodiments, polynucleotides are provided that comprise some or all of a polynucleotide sequence encoding an antibody as described herein and complements of such polynucleotides.

In other related embodiments, polynucleotide variants may have substantial identity to a polynucleotide sequence encoding an anti-IL-1β antibody described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence such as a sequence encoding an antibody described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically set forth herein.

In certain other related embodiments, polynucleotide fragments may comprise or consist essentially of various lengths of contiguous stretches of sequence identical to or complementary to a sequence encoding an antibody as described herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of a sequences the encodes an antibody, or antigen-binding fragment thereof, disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of a polynucleotide encoding an antibody described herein or at both ends of a polynucleotide encoding an antibody described herein.

In another embodiment, polynucleotides are provided that are capable of hybridizing under moderate to high stringency conditions to a polynucleotide sequence encoding an antibody, or antigen-binding fragment thereof, provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the polynucleotides described above, e.g., polynucleotide variants, fragments and hybridizing sequences, encode antibodies that bind IL-1β, or antigen-binding fragments thereof. In other embodiments, such polynucleotides encode antibodies or antigen-binding fragments, or CDRs thereof, that bind to IL-1β at least about 50%, at least about 70%, and in certain embodiments, at least about 90% as well as an antibody sequence specifically set forth herein. In further embodiments, such polynucleotides encode antibodies or antigen-binding fragments, or CDRs thereof, that bind to IL-1β with greater affinity than the antibodies set forth herein, for example, that bind quantitatively at least about 105%, 106%, 107%, 108%, 109%, or 110% as well as an antibody sequence specifically set forth herein.

As described elsewhere herein, determination of the three-dimensional structures of representative polypeptides (e.g., variant IL-1β-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within an antibody such that, for example, affinity is maintained or better affinity is achieved.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); Methods in Enzymology vol. 183, Academic Press, Inc., San Diego, Calif.; Higgins, D. G. and Sharp, P. M., *CABIOS* 5:151-153 (1989); Myers, E. W. and Muller W., CABIOS 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, Proc. Natl. Acad. Sci. USA 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an antibody as described herein. Some of these polynucleotides bear minimal sequence identity to the nucleotide sequence of the native or original polynucleotide sequence that encode antibodies that bind to IL-1β. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the antibodies described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the polynucleotide sequences that encode an antibody disclosed herein, or an antigen-binding fragment thereof, to alter one or more properties of the encoded polypeptide, such as the binding affinity of the antibody or the antigen-binding fragment thereof, or the function of a particular Fc region, or the affinity of the Fc region for a particular FcγR. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

In many embodiments, the nucleic acids encoding a subject monoclonal antibody are introduced directly into a host cell, and the cell incubated under conditions sufficient to induce expression of the encoded antibody. The antibodies of this disclosure are prepared using standard techniques well known to those of skill in the art in combination with the polypeptide and nucleic acid sequences provided herein. The polypeptide sequences may be used to determine appropriate nucleic acid sequences encoding the particular antibody disclosed thereby. The nucleic acid sequence may be optimized to reflect particular codon "preferences" for various expression systems according to standard methods well known to those of skill in the art.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

Antibodies or antigen-binding fragments thereof as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antigen-binding fragments in prokaryotic cells such as *E. coli* is well established in the art. For a review, see for example Pluckthun, A. Bio/Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies, and which further expresses or is capable of expressing a selected gene of interest, such as a gene encoding any herein described antibody. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as an IL-1β-specific antibody as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the antibodies that bind to IL-1β of the present disclosure, or sequences that have deletions from, additions to, and/or substitutions of one or more amino acid of an anti-IL-1β antibody. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-IL-1β antibody, useful fragments include, but are not limited to: a CDR region, especially a CDR3 region of the heavy or light chain; a variable region of a heavy or light chain; a portion of an antibody chain or just its variable region including two CDRs; and the like (see e.g., FIG. 1 and the sequences provided in the sequence listing)

Polypeptides may comprise a signal (or leader) sequence at the N-terminal end of the protein, which co-translationally or post-translationally directs transfer of the protein. The polypeptide may also be fused in-frame or conjugated to a linker or other sequence for ease of synthesis, purification or identification of the polypeptide (e.g., poly-His), or to enhance binding of the polypeptide to a solid support.

A peptide linker/spacer sequence may also be employed to separate multiple polypeptide components by a distance sufficient to ensure that each polypeptide folds into its secondary and/or tertiary structures, if desired. Such a peptide linker sequence can be incorporated into a fusion polypeptide using standard techniques well known in the art.

Certain peptide spacer sequences may be chosen, for example, based on: (1) their ability to adopt a flexible extended conformation; (2) their inability to adopt a secondary structure that could interact with functional epitopes on the first and second polypeptides; and/or (3) the lack of hydrophobic or charged residues that might react with the polypeptide functional epitopes.

In one illustrative embodiment, peptide spacer sequences contain, for example, Gly, Asn and Ser residues. Other near neutral amino acids, such as Thr and Ala, may also be included in the spacer sequence.

Other amino acid sequences which may be usefully employed as spacers include those disclosed in Maratea et al., Gene 40:39 46 (1985); Murphy et al., *Proc. Natl. Acad. Sci. USA* 83:8258 8262 (1986); U.S. Pat. No. 4,935,233 and U.S. Pat. No. 4,751,180.

Other illustrative spacers may include, for example, Glu-Gly-Lys-Ser-Ser-Gly-Ser-Gly-Ser-Glu-Ser-Lys-Val-Asp (Chaudhary et al., 1990, Proc. Natl. Acad. Sci. U.S.A. 87:1066-1070) and Lys-Glu-Ser-Gly-Ser-Val-Ser-Ser-Glu-Gln-Leu-Ala-Gln-Phe-Arg-Ser-Leu-Asp (Bird et al., 1988, Science 242:423-426).

In some embodiments, spacer sequences are not required when the first and second polypeptides have non-essential N-terminal amino acid regions that can be used to separate the functional domains and prevent steric interference. Two coding sequences can be fused directly without any spacer or by using a flexible polylinker composed, for example, of the pentamer Gly-Gly-Gly-Gly-Ser repeated 1 to 3 times. Such a spacer has been used in constructing single chain antibodies (scFv) by being inserted between VH and VL (Bird et al., 1988, Science 242:423-426; Huston et al., 1988, Proc. Natl. Acad. Sci. U.S.A. 85:5979-5883).

A peptide spacer, in certain embodiments, is designed to enable the correct interaction between two beta-sheets forming the variable region of the single chain antibody.

In certain illustrative embodiments, a peptide spacer is between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids.

In other illustrative embodiments, a peptide spacer comprises about 1, 5, 10, 15, 20, 25, 30, 35, 40, 45, 50 or more amino acids in length.

Amino acid sequence modification(s) of the antibodies described herein are contemplated. For example, it may be desirable to improve the binding affinity and/or other biological properties of the antibody. For example, amino acid sequence variants of an antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics (e.g., high affinity binding to IL-1β). The amino acid changes also may alter post-translational processes of the antibody, such as changing the number or position of glycosylation sites. Any of the variations and modifications described above for polypeptides of the present invention may be included in antibodies of the present invention.

The present disclosure provides variants of the antibodies disclosed herein. In certain embodiments, such variant antibodies or antigen-binding fragments, or CDRs thereof, bind to IL-1β at least about 50%, at least about 70%, and in certain embodiments, at least about 90% as well as an antibody sequence specifically set forth herein. In further embodiments, such variant antibodies or antigen-binding fragments, or CDRs thereof, bind to IL-1β with greater affinity than the antibodies set forth herein, for example, that bind quantitatively at least about 105%, 106%, 107%, 108%, 109%, or 110% as well as an antibody sequence specifically set forth herein.

In particular embodiments, a subject antibody may have: a) a heavy chain variable region having an amino acid sequence that is at least 80% identical, at least 95% identical, at least 90%, at least 95% or at least 98% or 99% identical, to the heavy chain variable region of an anti-IL-1β antibody described herein; and b) a light chain variable region having an amino acid sequence that is at least 80% identical, at least 85%, at least 90%, at least 95% or at least 98% or 99% identical, to the light chain variable region of an anti-IL-1β antibody described herein. The amino acid sequence of illustrative heavy and light chain regions are set forth in SEQ ID NOs:1-12).

In particular embodiments, the antibody may comprise: a) a heavy chain variable region comprising: i. a CDR1 region that is identical in amino acid sequence to the heavy chain CDR1 region of a selected antibody described herein; ii. a CDR2 region that is identical in amino acid sequence to the heavy chain CDR2 region of the selected antibody; and iii. a CDR3 region that is identical in amino acid sequence to the heavy chain CDR3 region of the selected antibody; and b) a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; wherein the antibody specifically binds a selected target (e.g., IL-1β). In a further embodiment, the antibody, or antigen-binding fragment thereof, is a variant antibody wherein the variant comprises a heavy and light chain identical to the selected antibody except for up to 8, 9, 10, 11, 12, 13, 14, 15, or more amino acid substitutions in the CDR regions of the VH and VL regions. In this regard, there may be 1, 2, 3, 4, 5, 6, 7, 8, or in certain embodiments, 9, 10, 11, 12, 13, 14, 15 more amino acid substitutions in the CDR regions of the selected antibody. Substitutions may be in CDRs either in the VH and/or the VL regions. (See e.g., Muller, 1998, Structure 6:1153-1167).

Determination of the three-dimensional structures of representative polypeptides (e.g., variant IL-1β-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007); Raman et al. Science 327:1014-1018 (2010). Some additional non-limiting examples of computer algorithms that may be used for these and related embodiments, such as for rational design of IL-1β-specific antibodies antigen-binding domains thereof as provided herein, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/. Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

In another embodiment of invention, the anti-IL-1β antibodies and humanized versions thereof are derived from rabbit monoclonal antibodies, and in particular are generated using RabMAb® technology. These antibodies are advantageous as they require minimal sequence modifications, thereby facilitating retention of functional properties after humanization using mutational lineage guided (MLG) humanization technology (see e.g., U.S. Pat. No. 7,462,697).

Thus, illustrative methods for making the anti-IL-1β antibodies of the present disclosure include the RabMab® rabbit monoclonal antibody technology described, for example, in U.S. Pat. Nos. 5,675,063 and 7,429,487. In this regard, in certain embodiments, the anti-IL-1β antibodies of the disclosure are produced in rabbits. In particular embodiments, a rabbit-derived immortal B-lymphocyte capable of fusion with a rabbit splenocyte is used to produce a hybrid cell that produces an antibody. The immortal B-lymphocyte does not detectably express endogenous immunoglobulin heavy chain and may contain, in certain embodiments, an altered immunoglobulin heavy chain-encoding gene.

Compositions and Methods of Use

The present disclosure provides compositions comprising the IL-1β-specific antibodies, antigen-binding fragments thereof and administration of such composition in a variety of therapeutic settings.

Administration of the IL-1β-specific antibodies described herein, in pure form or in an appropriate pharmaceutical composition, can be carried out via any of the accepted modes of administration of agents for serving similar utilities. The pharmaceutical compositions can be prepared by combining an antibody or antibody-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, prevents or delays the progression and/or metastasis of a cancer is considered effective.

In certain embodiments, the amount administered is sufficient to result in clinically relevant reduction in inflammatory and autoimmune symptoms of a particular disease indication known to the skilled clinician.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The IL-1β-specific antibody-containing compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described IL-1β-specific antibody in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of an antibody of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of an IL-1β-specific antibody as herein disclosed such that a suitable dosage will be obtained. Typically, this amount is at least 0.01% of the antibody in the composition. When intended for oral administration, this amount may be varied to be between 0.1 and about 70% of the weight of the composition. Certain oral pharmaceutical compositions contain between about 4% and about 75% of the antibody. In certain embodiments, pharmaceutical compositions and preparations according to the present invention are prepared so that a parenteral dosage unit contains between 0.01 to 10% by weight of the antibody prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises an IL-1β-specific antibody as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the antibody composition so as to facilitate dissolution or homogeneous suspension of the antibody in the aqueous delivery system.

The compositions may be administered in a therapeutically effective amount, which will vary depending upon a variety of factors including the activity of the specific compound (e.g., IL-1β-specific antibody) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the IL-1β-specific antibodies of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising antibodies of the invention and each active agent in its own separate pharmaceutical dosage formulation. For example, an antibody as described herein and the other active agent can be administered to the patient together in a single oral dosage composition such as a tablet or capsule, or each agent administered in separate oral dosage formulations. Similarly, an antibody as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising antibodies and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of anti-IL-1β antibody compositions of this disclosure in combination with one or more other therapeutic agents. Such therapeutic agents may be accepted in the art as a standard treatment for a particular disease state as described herein, such as rheumatoid arthritis, inflammation or cancer. Exemplary therapeutic agents contemplated include cytokines, growth factors, steroids, NSAIDs, DMARDs, anti-inflammatories, chemotherapeutics, radiotherapeutics, or other active and ancillary agents.

In certain embodiments, the anti-IL-1β antibodies disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the anti-IL-1β antibodies described herein. In one embodiment, the antibody is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®)), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the antibodies described herein are administered in conjunction with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

The compositions comprising herein described IL-1β-specific antibodies may be administered to an individual afflicted with a disease as described herein, including, but not limited to inflammatory and autoimmune disorders. In particular, the antibodies described herein are useful for the treatment of rheumatoid arthritis, diabetes, gout, cryopyrin-associated periodic syndrome, chronic obstructive pulmonary disorder and various cardiovascular diseases such as atherosclerosis and vasculitis. The present antibodies are useful for the treatment of autoimmune and inflammatory syndromes characterized by attacks of sterile inflammation of joints, serositis, fever, and skin lesions. Inflammatory disease include, but are not limited to, Crohn's disease, colitis, dermatitis, psoriasis, diverticulitis, hepatitis, irritable bowel syndrome (IBS), lupus erythematous, nephritis, Parkinson's disease, ulcerative colitis, multiple sclerosis (MS), Alzheimer's disease, arthritis, rheumatoid arthritis, asthma, and various cardiovascular diseases such as atherosclerosis and vasculitis. In one embodiment, the present disclosure provides a method of treating, reducing the severity of or preventing inflammation or an inflammatory disease by administering to a patient in need thereof a therapeutically effective amount of a herein disclosed compositions. The present compositions comprising anti-IL-1β antibodies are useful for treating autoimmune diseases such as arthritis (including rheumatoid arthritis, reactive arthritis), systemic lupus erythematosus (SLE), psoriasis and inflammatory bowel disease (IBD), encephalomyelitis, uveitis, myasthenia gravis, multiple sclerosis, insulin dependent diabetes, Addison's disease, celiac disease, chronic fatigue syndrome, autoimmune hepatitis, autoimmune alopecia, ankylosing spondylitis, ulcerative colitis, Crohn's disease, fibromyalgia, pemphigus vulgaris, Sjogren's syndrome, Kawasaki's Disease, hyperthyroidism/Graves disease, hypothyroidism/Hashimoto's disease, endometriosis, scleroderma, pernicious anemia, Goodpasture syndrome, Guillain-Barrë syndrome, Wegener's disease, glomerulonephritis, aplastic anemia (including multiply transfused aplastic anemia patients), paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis and rheumatic fever, Autoimmune Lymphoproliferative Syndrome (ALPS), Autoimmune Bullous Pemphigoid, Parkinson's, sarcoidosis, vitiligo, primary biliary cirrhosis, and autoimmune myocarditis.

For in vivo use for the treatment of human disease, the antibodies described herein are generally incorporated into a pharmaceutical composition prior to administration. A pharmaceutical composition comprises one or more of the antibodies described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compositions comprising IL-1β-specific antibodies as described herein may be prepared with carriers that protect the antibody against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Provided herein are methods of treatment using the antibodies that bind IL-1β. In one embodiment, an antibody of the present invention is administered to a patient having a disease involving inappropriate expression of IL-1β, which is meant in the context of the present disclosure to include diseases and disorders characterized by aberrant IL-1β expression or activity, due for example to alterations (e.g., statistically significant increases or decreases) in the amount of a protein present, or the presence of a mutant protein, or both. An overabundance may be due to any cause, including but not limited to overexpression at the molecular level, prolonged or accumulated appearance at the site of action, or increased (e.g., in a statistically significant manner) activity of IL-1β relative to that which is normally detectable. Such an overabundance of IL-1β can be measured relative to normal expression, appearance, or activity of IL-1β signalling events, and said measurement may play an important role in the development and/or clinical testing of the antibodies described herein.

Another embodiment provides a method for treating, inhibiting the progression of or prevention of any of a variety of inflammatory or autoimmune diseases by administering to a patient afflicted by one or more of these diseases a therapeutically effective amount of a herein disclosed IL-1β-specific antibody.

In another embodiment, anti-IL-1β antibodies of the present invention are used to determine the structure of bound antigen, e.g., conformational epitopes, which structure may then be used to develop compounds having or mimicking this structure, e.g., through chemical modeling and SAR methods.

Various other embodiments of the present invention relate, in part, to diagnostic applications for detecting the presence of cells or tissues expressing IL-1β. Thus, the present disclosure provides methods of detecting IL-1β in a sample, such as detection of cells or tissues expressing IL-1β. Such methods can be applied in a variety of known detection formats, including, but not limited to immunohistochemistry (IHC), immunocytochemistry (ICC), in situ hybridization (ISH), whole-mount in situ hybridization (WISH), fluorescent DNA in situ hybridization (FISH), flow cytometry, enzyme immuno-assay (EIA), and enzyme linked immuno-assay (ELISA).

ISH is a type of hybridization that uses a labeled complementary DNA or RNA strand (i.e., primary binding agent) to localize a specific DNA or RNA sequence in a portion or section of a cell or tissue (in situ), or if the tissue is small enough, the entire tissue (whole mount ISH). One having ordinary skill in the art would appreciate that this is distinct from immunohistochemistry, which localizes proteins in tissue sections using an antibody as a primary binding agent. DNA ISH can be used on genomic DNA to determine the structure of chromosomes. Fluorescent DNA ISH (FISH) can, for example, be used in medical diagnostics to assess chromosomal integrity. RNA ISH (hybridization histochemistry) is used to measure and localize mRNAs and other transcripts within tissue sections or whole mounts.

The term "epitope tagged" as used herein refers to a chimeric polypeptide comprising a polypeptide, such as an antibody or fragment of the present invention, fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues). In some embodiments, the epitope tag as found in a chimeric polypeptide described herein is useful, for example, for identifying and isolating the tagged proteins.

Various tag polypeptides and their respective antibodies are well known in the art. Examples include poly-histidine (HIS6; poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985); and the Herpes Simplex virus glycoprotein D (gD) tag and its antibody (Paborsky et al., Protein Engineering, 3(6):547-553 (1990)). Another example is the FLAG-peptide (Hopp et al., BioTechnology, 6:1204-1210 (1988)), which is recognized by an anti-FLAG M2 monoclonal antibody (Sigma, St. Louis, Mo.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Examples of other tag polypeptides include the KT3 epitope peptide (Martin et al., Science, 255:192-194 (1992)); an α-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)).

In various embodiments, the antibodies described herein are conjugated to a detectable label that may be detected directly or indirectly. In this regard, an antibody "conjugate" refers to an anti-IL-1β antibody that is covalently linked to a detectable label. In the present invention, DNA probes, RNA probes, monoclonal antibodies, antigen-binding fragments thereof, and antibody derivatives thereof, such as a single-chain-variable-fragment antibody or an epitope tagged antibody, may all be covalently linked to a detectable label. In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically or otherwise) signal that indicates the presence and/or concentration of the label in a sample. When conjugated to a antibody, the detectable label can be used to locate and/or quantify the target to which the specific antibody is directed. Thereby, the presence and/or concentration of the target in a sample can be detected by detecting the signal produced by the detectable label. A detectable label can be detected directly or indirectly, and several different detectable labels conjugated to different specific-antibodies can be used in combination to detect one or more targets.

Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

In some embodiments, the detectable label is conjugated to a nucleic acid polymer which comprises the first binding agent (e.g., in an ISH, WISH, or FISH process). In other embodiments, the detectable label is conjugated to an antibody which comprises the first binding agent (e.g., in an IHC process).

Examples of detectable labels which may be conjugated to antibodies used in the methods of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), .alpha.-naphtol pyronin (.alpha.-NP), o-dianisidine (OD), 5-bromo-4-chloro-3-indolylphosp-hate (BCIP), Nitro blue tetrazolium (NBT), 2-(p-iodophenyl)-3-p-nitropheny-I-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/-fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b—d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to the antibodies described herein or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.).

The invention further provides kits for detecting IL-1β or cells or tissues expressing IL-1β in a sample, wherein the kits contain at least one antibody, polypeptide, polynucleotide, vector or host cell as described herein. In certain embodiments, a kit may comprise buffers, enzymes, labels, substrates, beads or other surfaces to which the antibodies of the invention are attached, and the like, and instructions for use.

EXAMPLES

Example 1

Production and Humanization of Monoclonal Anti-IL-1β Antibodies

1 Antibody Production
1.1 Immunization

Three New Zealand white rabbits were immunized subcutaneously with 0.5 mg of recombinant human IL-1β in complete Freund's adjuvant (Sigma-Aldrich Corp., St. Louis, Mo.). After the initial immunization, animals were boosted 5 times with 0.25 mg IL-1β in incomplete Freund's adjuvant in a 3 week-interval. The rabbit with the highest serum titers and IL-1β neutralizing activity was intravenously boosted with 0.4 mg IL-1β in PBS four days before splenoectomy for cell fusion.

1.2 Antibody Generation

Splenocytes were harvested from the immunized rabbit and fused with rabbit plasmacytoma cells 240E-W2 using PEG4000 (Sigma Chemical, St. Louis, Mo.). After being selected by HAT (hypoxanthine, aminopterin, and thymidine), hybridoma clones growing in the original 96-well plates were transferred to new 96-well plates with a medium change. Hybridoma supernatants were collected and screened for specific antigen binding. Four hundred hybridomas that were positive in the ELISA binding assay were selected for functional screening.

1.3 Functional Screening of Hybridomas

For functional screening, the supernatant from the confirmed 400 positive clones in 24-well plates were tested for neutralizing IL-1β-induced TF-1 cell (human premyeloid cell line) proliferation. Sixty clones were found to neutralize IL-1β activity. The top 34 clones that neutralized IL-1β activity were further selected for molecular cloning and recombinant expression for further functional characterization.

1.4 Recombinant Anti-IL-1β Antibodies

DNA fragments of L chains and the variable region (VH) of H chains of rabbit IgG from the top 34 clones were amplified by PCR. The L chain fragment was cloned into pTT5 vector at Hind III and Not I sites and the VH fragment into the constant region of H chain built-in pTT5 vector at Hind III and Kpn I sites. For each hybridoma, three DNA clones of L or H chain were sequenced and the plasmid with a consensus sequence was identified and used for recombinant expression. To express the recombinant antibody, the L and H chain plasmids were co-transfected into 293-6E cells (National Research Council Canada). The supernatants were harvested 5 days later and quantified using an ELISA assay to measure the IgG concentration before functional assays.

1.5 Functional Screening of Recombinant Anti-IL-1β Antibodies

Neutralization of IL-1β-induced TF-1 cell proliferation was performed to rank the potency of recombinant antibodies. TF-1 cells cultured in RPMI 1640 with 10% FBS were treated with titrated doses of antibodies in the presence of 400 pg/ml of IL-1β. AlamarBlue was added to assess the cell proliferation after 3 days. The result was shown in following table (Table 1). Highlighted clones with higher activity were selected for further functional ranking with purified material.

TABLE 1

Neutralizing activity of antibodies to IL-1β induced TF-1 cell proliferation.

| Clone ID | IC 50 (ng/ml) |
| --- | --- |
| Q1 | >5.9 |
| Q2 | >5.9 |
| Q3 | >5.9 |
| Q4 | >5.9 |
| Q5 | >5.9 |
| Q6 | 0.95 |
| Q7 | >5.9 |
| Q8 | >5.9 |
| Q9 | >5.9 |
| Q10 | >5.9 |
| Q11 | >5.9 |
| Q12 | >5.9 |
| Q13 | >5.9 |
| Q14 | >5.9 |
| Q15 | >5.9 |
| Q16 | 1.43 |
| Q17* | 1.13 |
| Q18 | >5.9 |
| Q19 | >5.9 |
| Q20 | >5.9 |
| Q21 | >5.9 |
| Q22 | >5.9 |
| Q23 | >5.9 |
| Q24 | >5.9 |
| Q25 | >5.9 |
| Q26* | 0.54 |
| Q27 | >59. |
| Q28 | >5.9 |
| Q29 | 4.6 |
| Q30 | >5.9 |
| Q31 | >5.9 |
| Q32 | 0.74 |
| Q33 | 0.78 |
| Q34* | 0.55 |
| Control Mab | 5.99 |

*indicated identical DNA sequence of H chain and L chain.

1.6 Functional Ranking of Recombinant Anti-IL-1β Antibodies

Clones Q6, 16, 26, 32, 33 were selected for further functional analysis to assess their potency to neutralize IL-1β activity. All antibodies were expressed in 293-6E cells and the supernatants were purified through a protein A column and quantified after dialyzing against PBS buffer. FIG. 2 shows the dose-dependent inhibition of IL-1β-induced TF-1 cell proliferation. Anakinra was used as a positive control. The IC50 of each antibody was also calculated. All the clones exhibited more potent IL-1β neutralizing activity as compared to Anakinra. Clone Q26 showed the highest neutralizing potency.

1.7 Binding Affinity of Anti-IL-1β Antibodies to IL-1β

Antigen binding affinities of anti-IL-1β antibodies were measured by surface Plasmon resonance (SPR). The Kd of each antibody is shown in Table 2. Clone Q26 showed the highest binding affinity to IL-1β.

TABLE 2

Binding affinities of anti-IL-1β antibodies

| antibody | $k_a$ (1/Ms) | $k_d$ (1/s) | $K_D$ (nM) | Chi$^2$ |
|---|---|---|---|---|
| Q6 | 1.07E5 | 5.17E−5 | 0.483 | 9.56 |
| Q26 | 1.91E5 | 3.8E−5 | 0.199 | 8.66 |
| Q32 | 2.7E5 | 6.49E−5 | 0.241 | 1.96 |
| Q33 | 1.55E5 | 1.23E−4 | 0.793 | 0.376 |
| Q16 | 1.35E5 | 8.68E−5 | 0.644 | 0.176 |

1.8 Blocking IL-1β-Induced NFκB Nuclear Translocation

Figure 3:
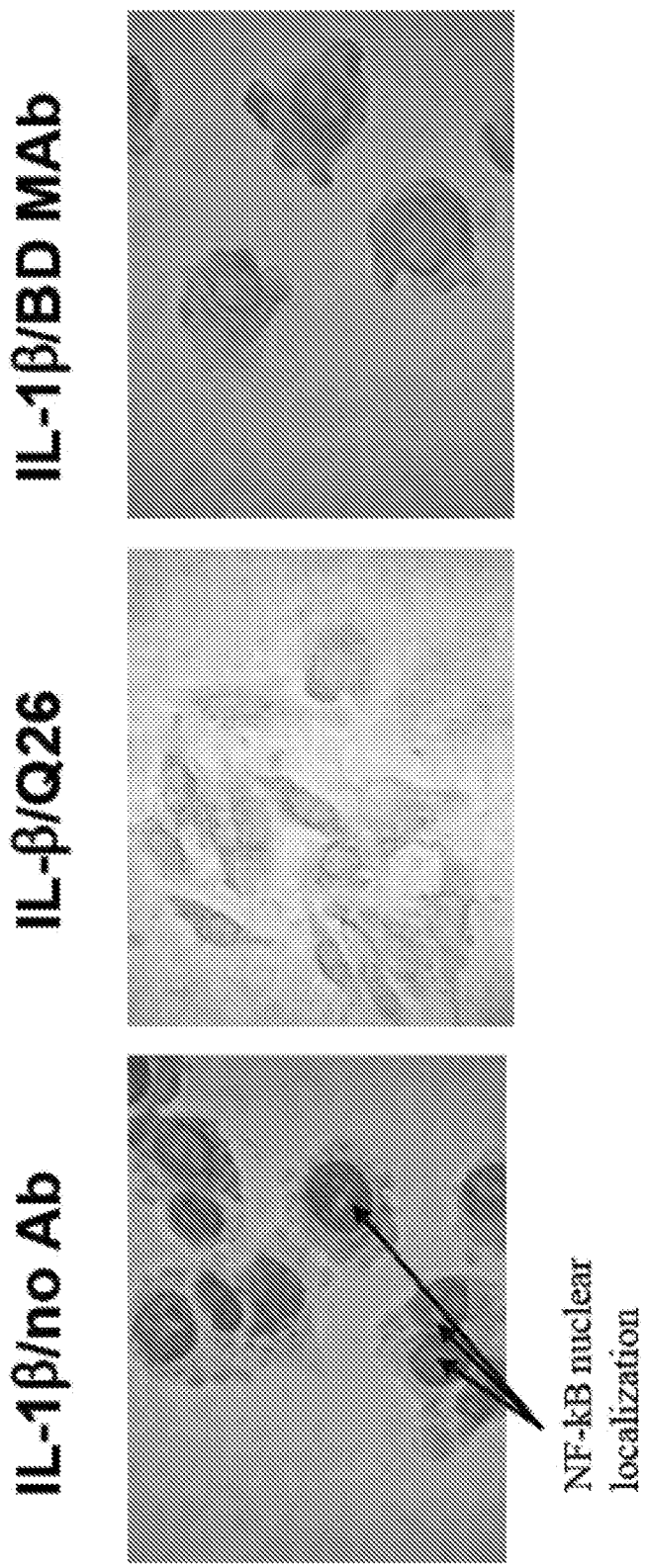
FIG. 3 shows inhibition of IL-1-β1-induced NF-κB nuclear translocation.

The nuclear translocation of NF-kB assay was performed to assess the activity of clone Q26 to block IL-1β-induced downstream signal. CHO/dhfr cells were treated with 10 ng/ml of IL-1β for 20 minutes. Then cells were fixed and NF-kB localization was detected with a mouse anti-NF-kB p65 (BD bioscience) and a secondary goat anti-mouse HRP antibody (Immunovision). FIG. 3 is a representative data showing that clone Q26 blocks the NF-kB nuclear translocation stimulated by IL-1β.

2. Antibody Humanization
2.1 Humanization Design

Clone Q26 was humanized using a proprietary mutational lineage guided (MLG) humanization technology. First, the heavy chain (VH) and light chain (VK) variable region sequences of clone Q26 were blasted against the human germline VH and VK database. The closest human germline sequences, VH3-66 and VK-L19 were identified as the template for clone Q26 humanization. Secondly, antibody sequences within the clone Q26 lineage were aligned. The lineage clones have similar sequences in CDRs and contain the same number of amino acid residues in the variable region. Third, the rabbit residues in the framework regions potentially involved in CDR contacts or inter-chain contacts were identified based on the knowledge from human and mouse antibodies. Residues considered not critical to the structural activity of the antibody based on the phylogenetic analysis were humanized. After MLG engineering, the frameworks of the humanized Q26 is 93.5% identical to the human germline frameworks. In addition, MLG humanization technology allowed further humanization in CDR1 of H chain and CDR3 of L chain, each differing from the parent rabbit antibody by one amino acid (see FIG. 1 and SEQ ID NOs:11 and 12.

2.2 Expression of Humanized Q26

DNA encoding humanized VK and VH of Q26 was synthesized by MCLab (South San Francisco, Calif., USA). The DNA fragment includes signal peptide and a Kozak sequence at the 5' end. To express the humanized Q26, the humanized VK fragment was cloned into human CK built-in pTT5 vector at Hind III and Nhe I. The humanized VH was cloned into human IgG1 CH built-in pTT5 vector at Hind III and BsiW I site. DNA and amino acid sequences of human CK and IgG1 CH were chosen for the constant region. Humanized Q26 was expressed in 293-6E cells, purified through a protein A column and quantified by UV280 after dialyzing against PBS buffer.

2.3 Humanized Q26 Retains Biological Activities

Figure 4:
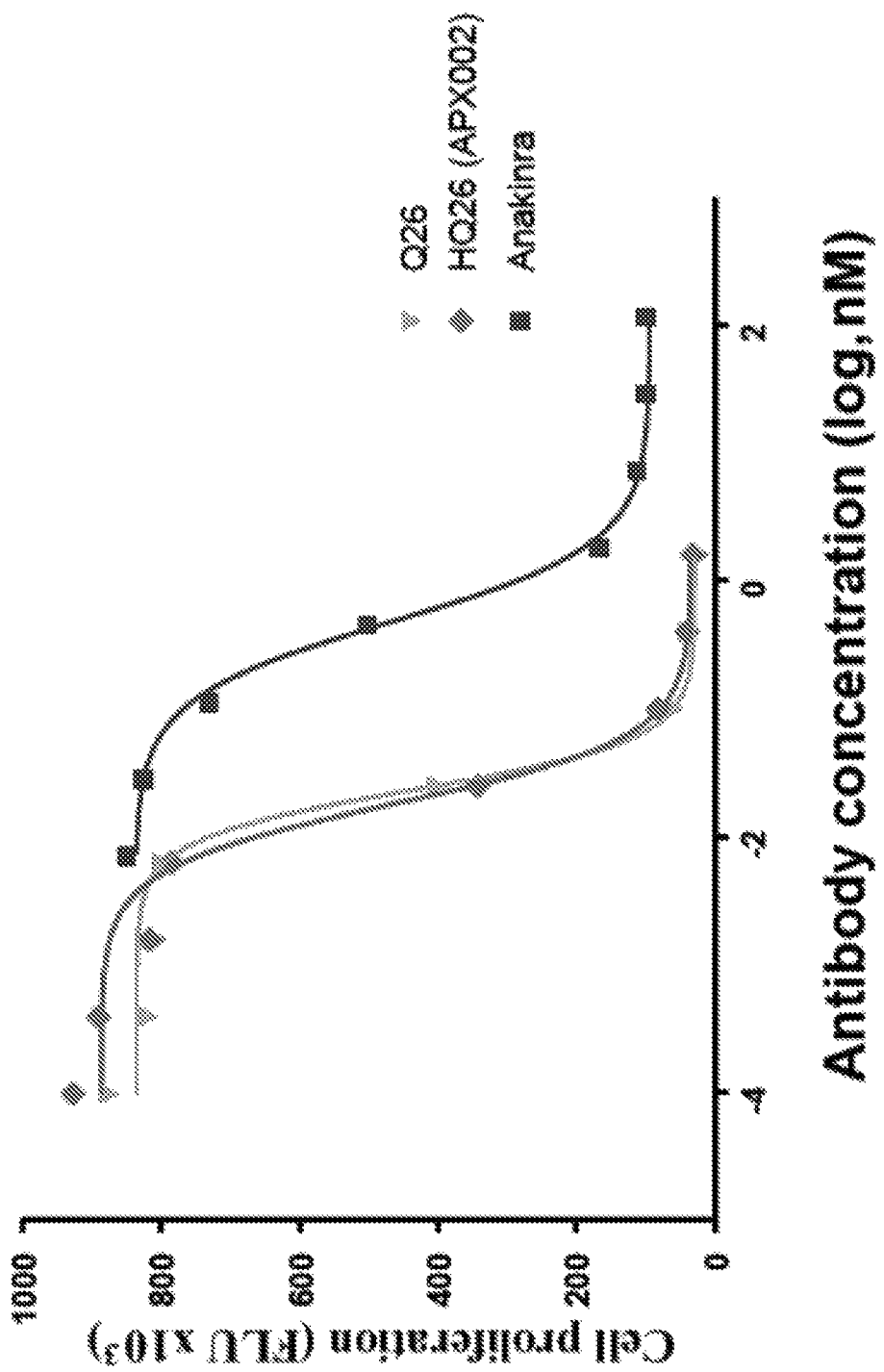
FIG. 4 shows the dose dependent inhibition of IL-1β stimulated TF-1 cells by humanized Q26 antibody.

The ability of humanized Q26 to inhibit IL-1β-induced TF-1 cell proliferation was examined. Humanized Q26 showed dose-dependent inhibition on IL-1β-stimulated TF-1 cell growth and exhibited similar potency as its parental rabbit Q26 (FIG. 4). Thus, humanized Q26 was chosen for further preclinical development and was named APX002.

3. Preclinical Development
3.1 In Vitro IL-1β Neutralizing Activity of APX002

Figure 5:
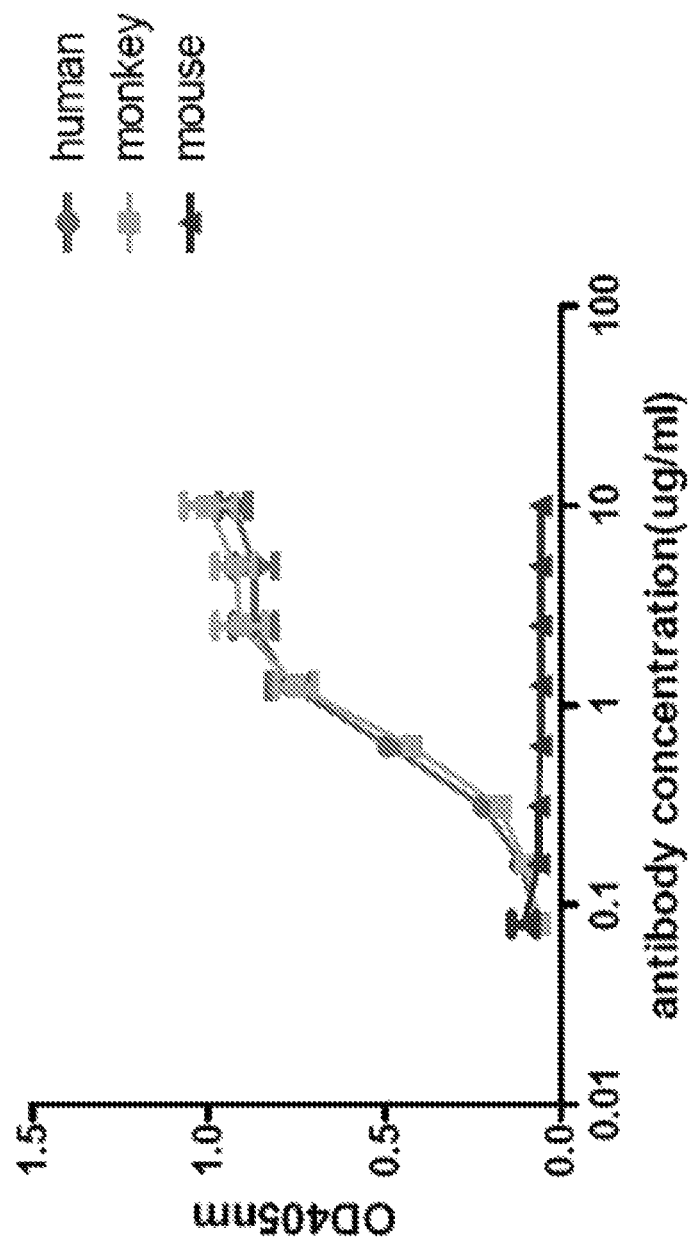
FIG. 5 shows cross reactivity results for monkey and mouse IL-1β.

APX002 is a humanized monoclonal antibody, initially identified from a rabbit hybridoma clone Q26. APX002 was selected as the lead because of its ability to bind specifically to human IL-1β and neutralize IL-1β related activities in vitro. It binds to IL-1β with an affinity of $1.99 \times 10_{-10}$M. In a cross-species reactivity assay, APX002 showed cross-reactivity with monkey IL-1β with similar affinity to human IL-1β, but did not cross-react with mouse IL-1β (FIG. 5).

3.2 Biological Effects of APX002 in an Ex Vivo Model

To further evaluate its biologic activity, APX002 was tested in an ex vivo assay using human peripheral blood cells. In this assay, the human whole blood cells from 4 donors were stimulated with *Staphylococcus epidermidis* in the presence of APX002. Upon binding to Toll like receptor (TLR), *Staphylococcus epidermidis* triggers IL-1β production, and then IL-1β induces downstream biological effects including production of other cytokines such as IL-6 and TNFα. Thus, IL-6 production can be used as readout to measure the ability of APX002 to block IL-1β. After 24 hours incubation, blood cells were lysed with Triton®-X to extract membrane and intracellular cytokines for measurement. As shown in table 3, APX002 strongly inhibited the production of IL-6 induced by *Staphylococcus epidermidis*. At both doses tested, APX002 is slightly more potent than Xoma-052, another anti-IL-1β antibody currently under clinical development.

TABLE 3

Inhibition of STAPH-induced IL-6 production by APX002 at 83 pM (upper) and 166 pM (lower). IL-6 was measured by ELISA kit. Xoma-052 (antibody against IL-1β) was used as a positive control.

| Antibody concentration | % inhibition of IL-6 production | | | | | |
|---|---|---|---|---|---|---|
| | Donor 1 | Donor 2 | Donor 3 | Donor 4 | Ave. | STDEV |
| APX002 12.5 ng/ml (83 pM) | 30 | 44 | 65 | 30 | 42 | 17 |
| Xoma-052 12.5 ng/ml (83 pM) | 49 | 14 | 46 | 48 | 39 | 17 |
| APX002 25 ng/ml (166 pM) | 45 | 61 | 84 | 40 | 58 | 20 |
| Xoma-052 25 ng/ml (166 pM) | 60 | 44 | 63 | 62 | 57 | 9 |

In other experiments, LPS (TLR ligand) was used to stimulate IL-1β-induced cytokine production using cultured human whole blood cells. Both high and low doses of APX002 inhibited LPS-induced TNFα and IL-6 production (Table 4). At the lower dose (83 pM), APX002 proved to be substantially more effective at inhibiting IL-6 and TNFα production than Xoma-052. At the higher dose (166 µM), APX002 exhibited similar inhibitory activity to that of Xoma-052.

TABLE 4

Inhibition of LPS-induced IL-6 and TNFα production at 83 pM (upper) and 166 pM (lower) by APX002. IL-6 and TNFα were measured by ELISA kits. Xoma-052 was used as a positive control.

| | % inhibition of production | | | | | |
|---|---|---|---|---|---|---|
| | IL-6 | | | TNF α | | |
| Antibody Concentration | Donor CAD | Donor E | Ave | Donor CAD | Donor E | Ave |
| APX002 12.5 ng/ml (83 pM) | 40 | 15 | 27.5 | 64 | 18 | 41 |
| Xoma-052 12.5 ng/ml (83 pM) | 5 | 20 | 12.5 | 0 | 14 | 7 |
| APX002 25 ng/ml (166 pM) | 52 | 29 | 40.5 | 81 | 13 | 47 |
| Xoma-052 25 ng/ml (166 pM) | 65 | 30 | 47.5 | 30 | 84 | 47 |

These ex vivo data using human whole blood cell cultures further confirmed the biological activity of APX002 as a potent IL-1β antagonist.

3.3 In Vivo Efficacy of APX002 in Disease Models.

The fact that APX002 does not cross-react with mouse IL-1β limited the use of mouse models to evaluate its in vivo pharmacology. As an alternative, two animal studies are used to test the in vivo efficacy of APX002.•In the human IL-1β-induced mouse model of joint inflammation, the NIH 3T3 fibroblast cell line producing high levels of hIL-1β are injected into right knee joints of DBA-1 mice to induce hIL-1β-dependent arthritis. APX002 is administered and tested in this model for efficacy in treating inflammation. Further, injection of monosodium urate (MSU) crystals into the monkey air pouch can elicit an acute inflammatory response similar to human gout. APX002 is administered and tested in this model for efficacy in treating gout.

REFERENCES

Lachmann, H J; Kone-Paut I, Kuemmerle-Deschner J B et al. (4 Jun. 2009). "Use of canakinumab in the cryopyrin-associated periodic syndrome". *New Engl J Med* 360 (23): 2416-25.

Wan, Yuet (29 Oct. 2009). "Canakinumab (Ilaris®) and rilonacept (Arcalyst®) approved in EU for treatment of cryopyrin-associated periodic syndrome". National electronic Library for Medicines.

Yasothan U, Kar S (2008). "Therapies for COPD". Nat Rev Drug Discov 7: 285. Dinarello C A (1994). "The interleukin-1 family: 10 years of discovery". *Faseb J.* 8 (15): 1314-25.

Abramson S B, Amin A. Blocking the effects of IL-1 in rheumatoid arthritis protects bone and cartilage. Rheumatology (Oxford). 2002 September; 41(9):972-80.

Gabay C, Lamacchia C, Palmer G. IL-1 pathways in inflammation and human diseases. Nat Rev Rheumatol. 2010 April; 6(4):232-41.

Chung Y, Chang S H, Martinez G J, Yang X O, Nurieva R, et al. (2009) Critical regulation of early Th17 cell differentiation by interleukin-1 signaling. Immunity 30: 576-587.

Smirnova M G, Kiselev S L, Gnuchev N V, et al. (2003). "Role of the pro-inflammatory cytokines tumor necrosis factor-alpha, interleukin-1 beta, interleukin-6 and interleukin-8 in the pathogenesis of the otitis media with effusion.". *Eur. Cytokine Netw.* 13 (2): 161-72.

Pickersgill L M, Mandrup-Poulsen T R. The anti-interleukin-1 in type 1 diabetes action trial—background and rationale. Diabetes Metab Res Rev. 2009 May; 25(4):321-4.

Marshak, S., et al. 1999. Impaired beta-cell functions induced by chronic exposure of cultured human pancreatic islets to high glucose. Diabetes. 48:1230-1236.

Maedler, K., et al. 2001. Glucose induces b-cell apoptosis via upregulation of the Fas receptor in human islets. Diabetes. 50:1683-1690.

Loweth, A. C., Williams, G. T., James, R. F., Scarpello, J. H., and Morgan, N. G. 1998. Human islets of Langerhans express Fas ligand and undergo apoptosis in response to interleukin-1 beta and Fas ligation. Diabetes. 47:727-732.

Darville, M. I., and Eizirik, D. L. 2001. Cytokine induction of Fas gene expression in insulin-producing cells requires the transcription factors NF-kappaB and C/EBP. Diabetes. 50:1741-1748.

Maedler K, Sergeev P, R is F, Oberholzer J, Joller-Jemelka H I, Spinas G A, Kaiser N, Halban P A, Donath M Y. Glucose-induced β cell production of IL-1β contributes to glucotoxicity in human pancreatic islets. J Clin Invest 2002, 110: 851-860.

Sauter N S, Schulthess F T, Galasso R, Castellani L W, Maedler K. The anti-inflammatory cytokine interleukin-1 receptor antagonist protects from high-fat diet-induced hyperglycemia. Endocrinology 2008, 149:2208-2218.

Smolen J S, Steiner G: Therapeutic strategies for rheumatoid arthritis. Nat Rev Drug Discov 2003, 2:473-488.

Dinarello C A: The IL-1 family and inflammatory diseases. Clin Exp Rheumatol 2002, 20:S1-S13.

Dinarello C A: Therapeutic strategies to reduce IL-1 activity in treating local and systemic inflammation. Curr Opin Pharmacol 2004, 4:378-385.

Dayer J M: The pivotal role of interleukin-1 in the clinical manifestations of rheumatoid arthritis. Rheumatology (Oxford) 2003, 42(suppl 2):ii3-ii10.

Cunnane G, Madigan A, Murphy E, Fitzgerald O, Bresnihan B: The effects of treatment with interleukin-1 receptor antagonist on the inflamed synovial membrane in rheumatoid arthritis. Rheumatology (Oxford) 2001, 40:62-69.

Bresnihan B, Cobby M: Clinical and radiological effects of anakinra in patients with rheumatoid arthritis. Rheumatology (Oxford) 2003, 42(suppl 2):ii22-ii28.

Martinon F et al. (2006) Gout-associated uric acid crystals activate the NALP3 inflammasome. Nature 440: 237-241

So A et al. (2007) A pilot study of IL-1 inhibition by anakinra in acute gout. Arthritis Res Ther 9: R28

Hoffman H M et al. (2001) Mutation of a new gene encoding a putative pyrin-like protein causes familial cold autoinflammatory syndrome and Muckle-Wells syndrome. Nat Genet 29: 301-305.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the

What is claimed is:

1. An isolated antibody, or an antigen-binding fragment thereof, that binds to IL-1β, comprising (i) a heavy chain variable region comprising the VHCDR1 region set forth in SEQ ID NO:3, the VHCDR2 region set forth in SEQ ID NO:4, and the VHCDR3 region set forth SEQ ID NO:5; and (ii) a light chain variable region comprising the VLCDR1 region set forth in SEQ ID NO:6, the VLCDR2 region set forth in SEQ ID NO:7, and the VLCDR3 region set forth in SEQ ID NO: 8; or (iii) a heavy chain variable region comprising the VHCDR1 region set forth in SEQ ID NO:11, the VHCDR2 region set forth in SEQ ID NO:4, and the VHCDR3 region set forth SEQ ID NO:5; and (iv) a light chain variable region comprising the VLCDR1 region set forth in SEQ ID NO:6, the VLCDR2 region set forth in SEQ ID NO:7, and the VLCDR3 region set forth in SEQ ID NO: 12.

2. The isolated antibody, or antigen-binding fragment thereof, of claim 1 wherein the heavy chain variable region comprises the amino acid sequence set forth in SEQ ID NO:1.

3. The isolated antibody, or antigen-binding fragment thereof, of claim 1 wherein the light chain variable region comprises the amino acid sequence set forth in SEQ ID NO:2.

4. The isolated antibody of claim 1, wherein the antibody is humanized.

5. The isolated antibody of claim 4, wherein the VH region comprises the amino acid sequence set forth in SEQ ID NO:9 and the VL region comprises the amino acid sequence set forth in SEQ ID NO:10.

6. The isolated antibody of claim 1 wherein the antibody is selected from the group consisting of a single chain antibody, a ScFv, a univalent antibody lacking a hinge region, and a minibody.

7. The isolated antibody of claim 1 wherein the antibody is a Fab or a Fab' fragment.

8. The isolated antibody of claim 1 comprising a human IgG constant domain.

9. The isolated antibody of claim 8 wherein the IgG constant domain comprises an IgG1 CH1 domain.

10. A composition comprising a physiologically acceptable carrier and a therapeutically effective amount of the isolated antibody or antigen-binding fragment thereof according to claim 1.

11. An isolated antibody, or an antigen-binding fragment thereof, that binds to IL-1β, comprising a heavy chain variable region comprising the amino acid sequence set forth in SEQ ID NO: 1.

12. The isolated antibody, or an antigen-binding fragment thereof, of claim 11 comprising a light chain variable region which comprises the amino acid sequence set forth in SEQ ID NO:2.

13. An isolated antibody, or an antigen-binding fragment thereof, that binds to IL-1β, comprising a light chain variable region comprising the amino acid sequence set forth in SEQ ID NO:2.

* * * * *